United States Patent
Sinha et al.

(10) Patent No.: US 12,357,576 B2
(45) Date of Patent: Jul. 15, 2025

(54) FORMULATIONS OF TRIPHENYL CALCILYTIC COMPOUNDS

(71) Applicant: CALCILYTIX THERAPEUTICS, INC., Palo Alto, CA (US)

(72) Inventors: Uma Sinha, San Francisco, CA (US); Ananth Sridhar, San Francisco, CA (US); Leena Prasad, San Francisco, CA (US); Ali Komeyli, San Francisco, CA (US)

(73) Assignee: CALCILYTIX THERAPEUTICS, INC., Palo Alto, CA (US)

( * ) Notice: Subject to any disclaimer, the term of this patent is extended or adjusted under 35 U.S.C. 154(b) by 0 days.

(21) Appl. No.: 18/216,536

(22) Filed: Jun. 29, 2023

(65) Prior Publication Data

US 2024/0074978 A1 Mar. 7, 2024

Related U.S. Application Data

(63) Continuation of application No. 17/392,720, filed on Aug. 3, 2021, now abandoned.

(60) Provisional application No. 63/061,050, filed on Aug. 4, 2020.

(51) Int. Cl.
| | | |
|---|---|---|
| *A61K 9/20* | (2006.01) | |
| *A61K 9/28* | (2006.01) | |
| *A61K 31/195* | (2006.01) | |

(52) U.S. Cl.
CPC .......... *A61K 9/2018* (2013.01); *A61K 9/2009* (2013.01); *A61K 9/2054* (2013.01); *A61K 9/2853* (2013.01); *A61K 31/195* (2013.01)

(58) Field of Classification Search
CPC .. A61K 9/2018; A61K 9/2009; A61K 9/2054; A61K 9/2853; A61K 31/195
See application file for complete search history.

(56) References Cited

U.S. PATENT DOCUMENTS

| | | |
|---|---|---|
| 7,304,174 B2 | 12/2007 | Shinagawa et al. |
| 2012/0301552 A1 | 11/2012 | Shinagawa et al. |
| 2016/0271095 A2 | 9/2016 | Riccardi et al. |
| 2021/0171474 A1 | 6/2021 | Wang et al. |
| 2022/0040112 A1 | 2/2022 | Sinha et al. |
| 2022/0041684 A1 | 2/2022 | Patterson |
| 2022/0087961 A1 | 3/2022 | Bruce et al. |

FOREIGN PATENT DOCUMENTS

| | | |
|---|---|---|
| EP | 1964548 A1 | 9/2008 |
| WO | WO-2021029517 A1 | 2/2021 |
| WO | WO-2022031666 A1 | 2/2022 |
| WO | WO-2022060987 A1 | 3/2022 |

OTHER PUBLICATIONS

Anonymous, Calcilytix Initiates Phase 2 Study of encaleret for ADH1, Sep. 21, 2021, pp. 1-6; retrieved form the Internet: UrL:https://bridgebio.com/news/bridgebio-pharmas-cacilytix-therapeutics-initiates-phase-2-study-of-encaleret-for-autosomal-dominant-hypocalcemia-type-1-adh1, retrieved on Dec. 13, 2021.

Cabal et al., A Semimechanistic Model of the Time-Course of Release of PTH Into Plasma Following Administration of the Calcilytic JTT-305/MK-5442 in Humans, Journal of Bone and Mineral Research, Aug. 2013, vol. 28, No. 8, pp. 1830-1836; DOI: 10.1002/jbmr.1900.

Chomsky-Higgins et al., Recombinant Parathyroid Hormone Versus Usual Care: Do the Outcomes Justify the Cost?, World Journal of Surgery, 2017, vol. 42, No. 2, pp. 431-436.

Dershem et al., Familial Hypocalciuric Hyercalcemia Type 1 and Autosomal-Dominant Hypocalcemia Type 1: Prevalence in a Large Healthcare Population, the American Journal of Human Genetics, 2020, pp. 1-26.

Dong et al., Calcilytic Ameliorates Abnormalities of Mutant Calcium Sensing Receptor (CaSR) Knock-In Mice Mimicking Autosomal Dominant Hypocalcemia (ADH), Journal of Bone and Mineral Research, Nov. 2015, vol. 30, No. 11, pp. 1980-1993; DOI: 10.1002/jbmr.2551.

Dong et al., Persistent Activation of Calcium-Sensing Receptor Suppresses Bone Turnover, Increases Microcracks, and Decreases Bone Strength: Increased Microcracks with Reduced Bone Strength in ADH1 Mice, JBMR® Plus, Jul. 1, 2019, vol. 3, No. 7, p. e10182.

(Continued)

*Primary Examiner* — Robert A Wax
*Assistant Examiner* — Olga V. Tcherkasskaya
(74) *Attorney, Agent, or Firm* — Mintz Levin Cohn Ferris Glovsky and Popeo, P.C.

(57) ABSTRACT

The present disclosure provides tablet formulations including a triphenyl calcilytic compound for the treatment of autosomal dominant hypocalcemia (ADH), where the compound is represented by formula (I):

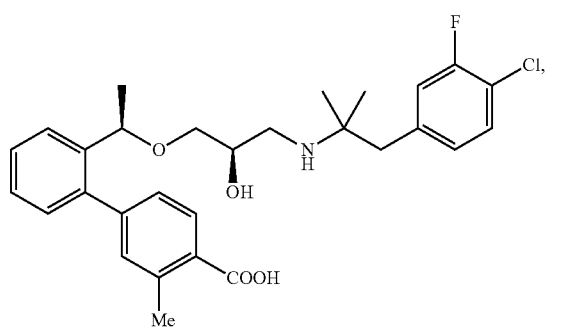

a solvate, a hydrate, a pharmaceutically acceptable salt, or a combination thereof.

11 Claims, 1 Drawing Sheet

(56) References Cited

OTHER PUBLICATIONS

European Patent Office, International Search Report and Written Opinion for International Application No. PCT/US2021/044295, mailed Oct. 20, 2021, 10 pages.
European Patent Office, International Search Report and Written Opinion for International Application No. PCT/US2021/050677, mailed Jan. 11, 2022, 12 pages.
Fisher et al., Pharmacodynamic Responses to combined treatment regimens with the calcium sensing receptor antagonist JTT-305/MK-5442 and alendronate in osteopenic ovariectomized rats, Mar. 5, 2012, Bone, vol. 50, No. 6, pp. 1332-1343.
Gafni et al., Transient Increased Calcium and Calcitriol Requirements After Discontinuation of Human Synthetic Parathyroid Hormone 1-34 (hPTH 1-34) Replacement Therapy in Hypoparathyroidism, Journal of Bone and Mineral Research, Nov. 2015, vol. 30, No. 11, pp. 2112-2118; DOI: 10.1002/jbmr.2555.
Gafni et al., A Phase 2B, Open-Label, Dose-Ranging Study of Encaleret (CLTX-305) in Autosomal Dominant Hypocalcemia Type 1 (ADH1), Journal of Endocrine Society, Apr.-May 2021, vol. 5, Issue Supplement_1, pp. A253-S254.
Gafni et al., The Effects of Encaleret (CLTX-305) on Mineral Physiology in Autosomal Dominant Hypocalcemia Type 1 ADH1 Demonstrate Proof-of-Concept: Early Results From an Ongoing Phase 2b, Open-Label, Dose-Ranging Study, Journal of the Endocrine Society, Apr.-May 2021, vol. 5, Issue Supplement 1, p. A269.
Gafni et al, Efficacy and Safety of Encaleret in Autosomal Dominant Hypocalcemia Type 1, The New England Journal of Medicine, Sep. 28, 2023, vol. 389, pp. 1245-1247.
Gunn et al., Clinical and laboratory features of calcium-sensing receptor disorders: a systematic review, Ann Clin Biochem, 2004, vol. 41, pp. 441-458. DOI: 10.1258/0004563042466802.
Hannan et al., Identification of 70 calcium-sensing receptor mutations in hyper- and hypo-calcaemic patients: evidence for clustering of extracellular domain mutations at calcium-binding sites, Human Molecular Genetics, 2012, vol. 21, No. 12, pp. 2768-2778; DOI: 10.1093/hmg/dds105.
Hannan et al., The Calcilytic Agent NPS 2143 Rectifies Hypocalcemia in a Mouse Model With an Activating Calcium-Sensing Receptor (CaSR) Mutation: Relevance to Autosomal Dominant Hypocalcemia Type 1 (ADH1), Endocrinology, Sep. 2015, vol. 156, No. 9, pp. 3114-3121; Doi: 10.1210/en.2015-1269.
Hannan et al., Calcimimtic and calcilytic therapies for inherited disorders of the calcium-sensing receptor signaling pathway, Bristish Journal of Pharmacology, 2018, vol. 175, pp. 4083-4094.
Hannan et al., The calcium-sensing receptor in physiology and in calcitropic diseases, Nature Reviews | Endocrinology, Jan. 2019, vol. 15, No. 1, pp. 33-51.
Hofer et al., Extracellular Calcium Sensing and Signalling, Nature Reviews, Molecular Cell Biology, Jul. 2003, vol. 4, No. 7, pp. 530-538; DOI: 10.1038/nrm1154.
Holick, Michael R., Vitamin D Status: Measurement, Interpretation and Clinical Application, National Institutes of Health, Ann. Epidemiol., Feb. 2009, 19(2), pp. 73-78.
Institute of Medicine, Dietary Reference Intakes for Calcium and Vitamin D, Washington, D.C.: the National Academies Press, Chapter 5, 2011, pp. 345-402.
International Search Report and Written Opinion in International Application No. PCT/US2021/044295, mailed Oct. 20, 2021, 10 pages.
International Search Report and Written Opinion in International Application No. PCT/US2021/050677, mailed Jan. 11, 2022, 12 pages.

Khan et al., Standards of care for hypoparathyroidism in adults; a Canadian and International consensus, European Journal of Endocrinology, 2019 (published online 2018), vol. 180, pp. 1-23; DOI: 10.1530/EJE-18-0609.
Kimura et al., JTT-305, an orally active calcium-sensing receptor antagonist, stimulates transient parathyroid hormone release and bone formation in ovariectomized rats, European Journal of Pharmacology, 2011, 668: 331-336.
Li et al., The good, the bad, and the ugly of calcium supplementation: a review of calcium intake on human health, Clinical Interventions in Aging, 2018, vol. 13, pp. 2443-2452; DOI: 10.2147/CIA.S157523.
Mannstadt et al., Efficacy and safety of recombinant human parathyroid hormone (1-84) in hypoparathyroidism (REPLACE): a double-blind, placebo-controlled, randomised, phase 3 study, The Lancet Diabetes & Endocrinology, published online Oct. 7, 2013, vol. 1, No. 4, pp. 275-283. DOI: 10.1016/S2213-8587(13)70106-2.
Mayr et al., Activating Calcium-Sensing Receptor Mutations: Prospects for Future Treatment with Calcilytics, Trends in Endocrinology and Metabolism, Sep. 2016, vol. 27, No. 9, pp. 643-652.
Nemeth et al., Calcimimetic and Calcilytic Drugs: Feats, flops, and Futures, Calcified Tissue International, 2016, Aug. 20, 2015, vol. 98, No. 4, pp. 341-358.
Ponce De León-Ballesteros et al., Mid-Term and Long-Term Impact of Permanent Hypoparathyroidism After Total Thyroidectomy, World Journal of Surgery, published online Apr. 22, 2020, vol. 44, pp. 2692-2698; DOI: 10.1007/S00268-020-05531-0.
Ritschel et al., Die Tablette, Jan. 1, 2022, 58 pages.
Roberts et al., Treatment of Autosomal Dominant Hypocalcemia Type 1 With the Calcilytic NPSP795 (SHP635), Journal of Bone and Mineral Research, 2019, pp. 1-10; DOI: 10.1002/jbmr.3747.
Roszko et al., Autosomal Dominant Hypocalcemia (Hypoparathyroidism) Types 1 and 2, Frontiers in Physiology, Oct. 18, 2016, vol. 7, No. 458, pp. 1-7; DOI: 10.3389/fphys.2016.00458.
Shrestha et al., A mathematical model of parathyroid hormone response to acute changes in plasma ionized calcium concentration in humans, Mathematical Biosciences, 2010, vol. 226, No. 1, pp. 46-57; DOI: 10.1016/j.mbs.2010.04.001.
Vahe et al., Diseases associated with calcium-sensing receptor, Orphanet Journal of Rare Diseases, 2017, 12:19, 9 pages.
Winer et al., Synthetic Human Parathyroid Hormone 1-34 Replacement Therapy: A Randomized Crossover Trial Comparing Pump Versus Injections in the Treatment of Chronic Hypoparathyroidism, The Journal of Clinical Endocrinology and Metabolism, 2012, vol. 97, No. 2, pp. 391-399; DOI: 10.1210/jc.2011-1908.
Winer et al., Effects of Pump versus Twice-Daily Injection Delivery of Synthetic Parathyroid Hormone 1-34 in Children with Severe Congenital Hypoparathyroidism, The Journal of Pediatrics, 2014, vol. 165, No. 3, pp. 556-563.e1; DOI: 10.1016/j.jpeds.2014.04.060.
Anonymous, Phase 2 Study of the PTH-Independent Effects of Encaleret on Mineral Homeostasis in Subjects with Post-Surgical Hypoparathyroidism (PSH), Record History, Feb. 17, 2023, ver. 1, 16 pages, retrieved from the Internet, URL:https://clinicaltrials.gov/study/NCT05735015?tab=history&a1#version-content-panel.
Gafni et al., The Effects of Encaleret (CLTX-305) on Mineral Physiology in Autosomal Dominant Hypocalcemia Type 1 (ADH1) Demonstrate Proof-of-Concept: Early Results From an Ongoing Phase 2b, Open-Label, Dose-Ranging Study, Journal of the Endocrine Society, May 3, 2021, 3 pages, retrieved from the Internet: URL:https://www.ncbi.nlm.nih.gov/pmc/articles/PMC8090084/pdf/bvab048.545.pdf.
International Search Report and Written Opinion in International Application No. PCT/US2024/025390, mailed Aug. 1, 2024, 11 pages.

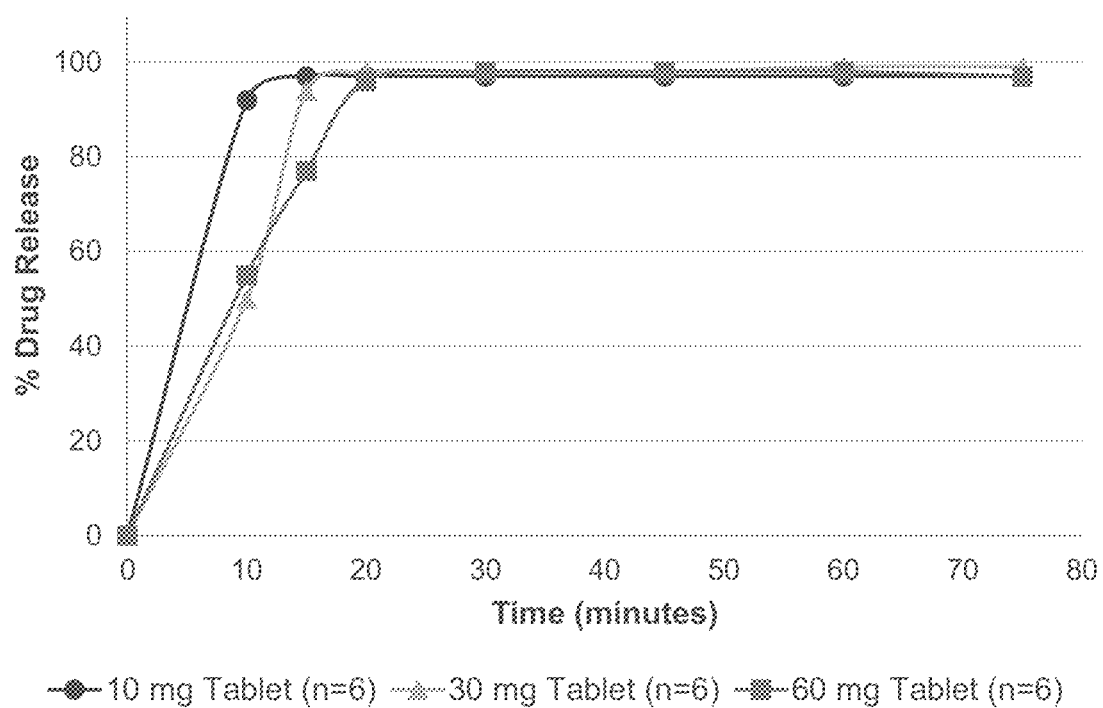

FORMULATIONS OF TRIPHENYL CALCILYTIC COMPOUNDS

CROSS-REFERENCES TO RELATED APPLICATIONS

This application is a continuation of U.S. application Ser. No. 17/392,720, filed on Aug. 3, 2021, which claims priority benefit to U.S. Provisional Application No. 63/061,050 filed Aug. 4, 2020, which is incorporated herein by reference in its entirety for all purposes.

BACKGROUND

Autosomal dominant hypocalcemia Type 1 (ADH1) is a rare disorder of systemic calcium homeostasis caused by activating mutations of the calcium-sensing receptor (CaSR) gene leading to hypocalcemia (Hannan et al. *Human Molecular Genetics*, 2012, 21 (12), p. 2768-2778; and Hofer et al., *Nature Reviews: Molecular Cell Biology*, 2003, 4 (7), p. 530-538). The CaSR plays the dominant role in regulating systemic calcium homeostasis by controlling parathyroid hormone (PTH) secretion and urinary calcium excretion in response to variations in blood calcium levels (Hofer et al., *Nature Reviews: Molecular Cell Biology*, 2003; and Gunn et al., *Ann. Clin. Biochem.*, 2004, 41 (Pt 6): p. 441-58). Negative allosteric modulators of the CaSR, (so-called calcilytic agents) may represent a potential targeted therapy for ADH1.

The prevalence of ADH1 is uncertain and has previously been estimated to have a prevalence of 1 per 70,000 (Gunn et al., *Ann. Clin. Biochem.*, 2004) or 3.9 per 100,000 (Dershem et al., *Am. J Hum. Genet.*, 2020); however, the disease is recognized as rare by the National Institutes of Health (NIH) Office of Rare Disease Research (Genetic and Rare Disease (GARD) Number: 2877) and Orphanet (Orpha Number: 428).

ADH1 is characterized by variable degrees of hypocalcemia with abnormally low levels of parathyroid hormone (PTH), hyperphosphatemia, and low magnesium levels usually with persistent hypercalciuria (Roszko et al., *Frontiers in Physiology*, 2016, 7, p. 458). Symptoms of hypocalcemia most commonly include paresthesia, muscle spasms, cramps, tetany, and circumoral numbness, and can be of variable intensity including inducing seizures. Hypocalcemia can also present with laryngospasm, neuromuscular irritability, cognitive impairment, personality disturbances, prolonged QT intervals, electrocardiographic changes that mimic myocardial infarction, and/or heart failure.

In patients with ADH1, hypocalcemia occurs primarily due to increased sensitivity of the CaSR to extracellular ionized calcium which suppresses iPTH secretion and leads to lower levels of 1,25-dihydroxyvitamin D3 (decreasing calcium absorption from the gut) and lower levels of calcium reabsorption in the kidney (leading to hypercalciuria). Hypercalciuria is increased based on two mechanisms: reduced PTH-mediated reabsorption of calcium from the primary renal filtrate, and further decreased calcium resorption in the distal renal tubules where the mutated CaSR is exposed to high calcium concentrations. Furthermore, standard treatment with oral calcium and calcitriol (e.g., 1,25-dihydroxyvitamin D3) supplementation tends to worsen hypercalciuria which is associated with long-term morbidity such as nephrolithiasis, nephrocalcinosis, and chronic kidney disease that can progress to renal failure (Khan et al., *European Journal of Endocrinology*, 2018; and Li et al., *Clinical Interventions in Aging*, 2018, 13, p. 2443-2452).

For this reason, the consensus approach to management of ADH1 is to balance oral supplementation of calcium and calcitriol with the known high risk for renal calcifications, kidney stones and kidney failure (Roszko et. al., *Frontiers in Physiology*, 2016). This means the healthcare provider must help the patient find a regimen that can maintain the lowest serum calcium concentrations compatible with symptom relief to minimize hypercalciuria. Thiazide diuretics are sometimes added for their modest urinary calcium lowering effects.

Experimental treatment with PTH(1-34) in ADH1 subjects was able to correct serum calcium but did not abrogate hypercalciuria (Winer et al., *The Journal of Clinical Endocrinology and Metabolism*, 2012, 97 (2), p. 391-399; Winer et al., *The Journal of Pediatrics*, 2014, 165 (3), 556-63; and Gafni et al., *Journal of Bone and Mineral Research*, 2015, 30 (11), p. 2112-2118). Exogenous PTH(1-84) is approved for the orphan indication of hypoparathyroidism but the clinical study in patients with established hypoparathyroidism that supported approval excluded patients with hypoparathyroidism due to calcium sensing receptor mutations (Chomsky et al., *World Journal of Surgery*, 2018, 42 (2), p. 431-436; and Natpara Product Insert).

Triphenyl calcilytic compounds refer to a class of compounds having a calcium-sensing receptor antagonistic action, as disclosed in U.S. Pat. No. 7,304,174 and represented by the following formula:

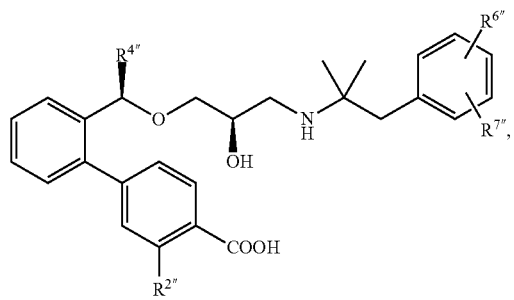

wherein $R^{2''}$ is a $C_{1-6}$ alkyl group; $R^{4''}$ is a methyl group or a cyclopropyl group; $R^{6''}$ is a halogen atom or a $C_{1-6}$ alkyl group; and $R^{7''}$ is a hydrogen atom, a halogen atom, a $C_{1-6}$ alkyl group, a $C_{1-6}$ alkoxy group, or a halo $C_{1-6}$ alkyl group, an optically active form thereof, a pharmaceutically acceptable salt thereof, or an optically active form of the salt thereof. In particular, the triphenyl calcilytic compound is represented by formula (I):

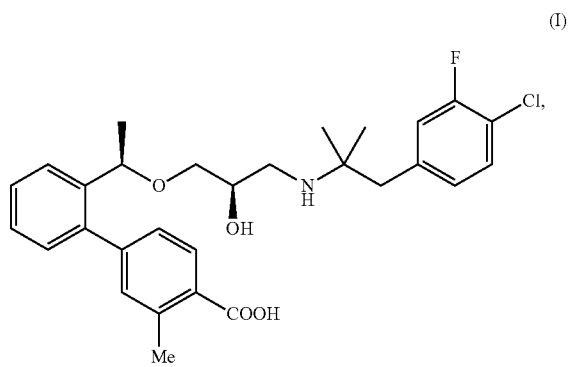 [SMILES: Cc1cc(-c2ccccc2[C@@H](C)OC[C@H](O)CNC(C)(C)Cc2ccc(Cl)c(F)c2)ccc1C(=O)O]

(I)

a solvate, a hydrate, a pharmaceutically acceptable salt, or a combination thereof. In certain embodiments, the compound of formula (I) is CLTX-305 represented by the formula:

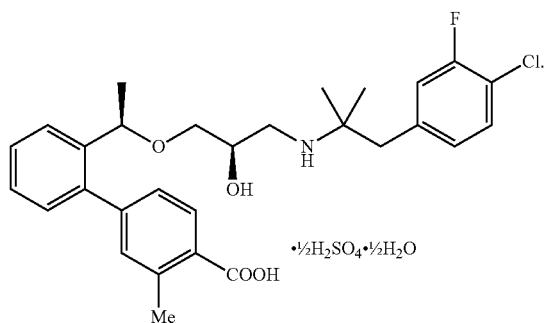 [SMILES: Cc1cc(-c2ccccc2[C@@H](C)OC[C@H](O)CNC(C)(C)Cc2ccc(Cl)c(F)c2)ccc1C(=O)O]

The compound of formula (I) or CLTX-305 may prove to be a therapy uniquely targeted to the underlying pathogenesis of altered calcium homeostasis in patients with ADH1 where resetting the CaSR "set-point" might normalize serum calcium with minimal requirements for oral supplementation and without increasing the risk of iatrogenic chronic hypercalciuria.

As such, there exists a need for the development of formulations including the compound of formula (I), in particular CLTX-305, which can be administered orally to treat ADH1.

SUMMARY

The present disclosure provides formulations including a calcium-sensing receptor antagonistic action, such as compounds of formula (I) provided herein. The present disclosure also provides methods of treating ADH1 using a formulation provided herein.

Accordingly, in a first aspect, the present disclosure provides a tablet formulation. The tablet formulation includes:

a) a compound represented by formula (I):

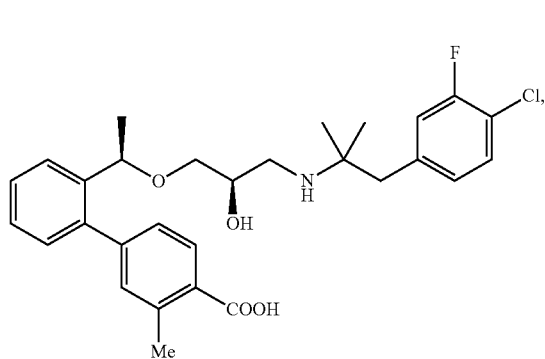

a solvate, a hydrate, a pharmaceutically acceptable salt, or a combination thereof; and
b) one or more pharmaceutically acceptable excipients selected from one or more fillers, one or more glidants, one or more disintegrants, one or more surfactants, one or more binders, one or more lubricants, and a combination thereof,
wherein the compound is present in an amount of at least about 12% by weight, on a salt-free and anhydrous basis.

In a second aspect, the present disclosure provides a tablet formulation as a common blend formulation across all dosage strengths. The common blend tablet formulation includes:

a) CLTX-305 represented by the formula:

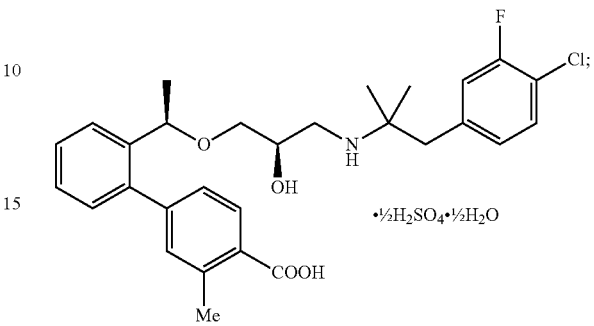

and
b) seven or more pharmaceutically acceptable excipients comprising a first filler, a second filler, a glidant, a disintegrant, a surfactant, a binder, and a lubricant, wherein:
CLTX-305 is present in an amount of from about 13% to about 30% by weight;
the first filler is mannitol;
the second filler is a microcrystalline cellulose;
the glidant is colloidal silicon dioxide;
the disintegrant is croscarmellose sodium;
the surfactant is one or more sucrose fatty acid esters comprising sucrose palmitate;
the binder is hydroxypropyl methylcellulose;
the lubricant is magnesium stearate; and
a ratio of the compound by weight to a total weight of the seven or more pharmaceutically acceptable excipients is constant across two or more dosage strengths.

In a third aspect, the present disclosure provides a method of treating autosomal dominant hypocalcemia type 1 (ADH). The method includes administering to a subject in need thereof, an effective amount of a tablet formulation provided herein, such as a tablet formulation comprising the compound of formula (I), or a solvate, a hydrate, a pharmaceutically acceptable salt, or a combination thereof (e.g., CLTX-305); and one or more pharmaceutically acceptable excipients selected from one or more fillers, one or more glidants, one or more disintegrants, one or more surfactants, one or more binders, one or more lubricants, and a combination thereof, wherein the compound is present in an amount of at least about 12% by weight, on a salt-free and anhydrous basis.

BRIEF DESCRIPTION OF THE DRAWINGS

FIG. 1 shows dissolution profiles of tablets including 10 mg, 30 mg, and 60 mg of CLTX-305.

DETAILED DESCRIPTION

I. General

The present disclosure provides a tablet formulation including a triphenyl calcilytic compound of formula (I), or a solvate, a hydrate, a pharmaceutically acceptable salt, or a combination thereof (e.g., CLTX-305), where the formulation may be a common blend formulation and wherein the ratio of the compound to one or more excipients may be maintained constant across a range of dosage strengths. For example, in some embodiments, a formulation containing about 14.3% of CLTX-305 can be successfully prepared as tablets. Various dose strengths (e.g., 10 milligrams (mg), 30 mg, and 60 mg of CLTX-305 per tablet) meet the necessary stability and pharmacokinetic requirements for oral formulations. The tablet formulations provided herein may be well suited for oral administration to human and animal subjects alike for the treatment of autosomal dominant hypocalcemia type 1 (ADH1).

II. Definitions

Unless specifically indicated otherwise, all technical and scientific terms used herein have the same meaning as commonly understood by those of ordinary skill in the art to which the present disclosure relates. In addition, any method or material similar or equivalent to a method or material described herein can be used in the practice of the compositions and methods described herein. For purposes of the present disclosure, the following terms are defined.

"Tablet" refers to solid pharmaceutical formulations with or without a coating. The term "tablet" also refers to solid pharmaceutical formulations having one, two, three or even more layers, wherein each of the before mentioned types of tablets may be with or without one or more coatings. In some embodiments, tablets of the present disclosure can be prepared by roller compaction or other suitable means known in the art. The term "tablet" also comprises mini, melt, chewable, effervescent, and orally disintegrating tablets. In some embodiments, the tablets provided herein include CLTX-305 and one or more pharmaceutically acceptable excipients selected from one or more fillers, one or more binders, one or more glidants, one or more disintegrants, one or more surfactants, one or more binders, one or more lubricants, and a combination thereof. In some embodiments, the tablets provided herein further comprise a coating agent. For the purposes of calculating percent weight of a tablet formulation, the amount of coating agent is not included in the calculation. That is, the percent weights reported herein are of the uncoated tablet.

"Pharmaceutically acceptable excipient" refers to a substance that aids the administration of an active agent to and/or absorption by a subject. Pharmaceutically acceptable excipients useful in the present disclosure include, but are not limited to, binders, fillers, glidants, disintegrants, surfactants, lubricants, coatings, sweeteners, flavors, and colors.

"Administering" refers to therapeutic provision of a formulation to a subject, such as by oral administration.

"Patient" or "subject" refers to a living organism suffering from or prone to a disease or condition that can be treated by administration of a pharmaceutical composition as provided herein. Non-limiting examples include humans, non-human primates (e.g., monkeys), goats, pigs, sheep, cows, deer, horses, bovines, rats, mice, rabbits, hamsters, guinea pigs, cats, dogs, and other non-mammalian animals. In some embodiments, the subject is human.

"Therapeutically effective amount" refers to an amount of a compound or of a pharmaceutical composition useful for treating or ameliorating an identified disease or condition, or for exhibiting a detectable therapeutic or inhibitory effect. The exact amounts will depend on the purpose of the treatment, safety, and response of the subject, and will be ascertainable by, clinicians, pharmacists, and the like (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Treat", "treating" and "treatment" refer to any indicia of success in the treatment or amelioration of an injury, pathology, or condition, or a symptom thereof, including any objective or subjective parameter such as abatement; remission; diminishing of symptoms or making the injury, pathology, or condition more tolerable to the patient; slowing in the rate of degeneration or decline; making the final point of degeneration less debilitating; and improving a patient's physical or mental well-being. The treatment or amelioration of symptoms can be based on objective or subjective parameters including the results of a physical examination, assay (e.g., analysis of a fluid of a subject, such as blood, plasma, or urine), imaging analysis, neuropsychiatric exams, and/or a psychiatric evaluation.

"About" means a range of values including the specified value, which a person of ordinary skill in the art would consider reasonably similar to the specified value. In some embodiments, the term "about" means within a standard deviation using measurements generally acceptable in the art. In some embodiments, about means a range extending to +/−10% of the specified value. In some embodiments, about means the specified value.

"Salt" refers to acid or base salts of the compounds of the present disclosure. Illustrative examples of pharmaceutically acceptable acid addition salts are mineral acid (hydrochloric acid, hydrobromic acid, phosphoric acid, and the like) salts and organic acid (acetic acid, propionic acid, glutamic acid, citric acid and the like) salts. Examples of pharmaceutically acceptable base addition salts include sodium, potassium, calcium, ammonium, organic amino, or magnesium salt, or a similar salt. It is understood that the pharmaceutically acceptable salts are non-toxic. Additional information on suitable pharmaceutically acceptable salts can be found in Remington's Pharmaceutical Sciences, 17th Edition, 1985, Mack Publishing Company, Easton, Pa., which is incorporated herein by reference.

"Solvate" refers to a compound provided herein or a salt thereof, that further includes a stoichiometric or non-stoichiometric amount of solvent bound by non-covalent intermolecular forces. Where the solvent is water, the solvate is a hydrate.

"Hydrate" refers to a compound provided herein or a salt thereof, that is complexed with a water molecule. The compounds or salts thereof of the present disclosure can be complexed with ½ water molecule or from 1 to 10 water molecules.

Unless specifically indicated otherwise, the content of the compound of formula (I) in the tablet formulation is calculated based on the normalized weight of the compound of formula (I) on a salt-free and anhydrous basis. That is, the salt and/or water content in the compound of formula (I) is not included in the calculation.

III. Formulations

The present disclosure provides a tablet formulation. The tablet formulation includes:
a) a compound represented by formula (I):

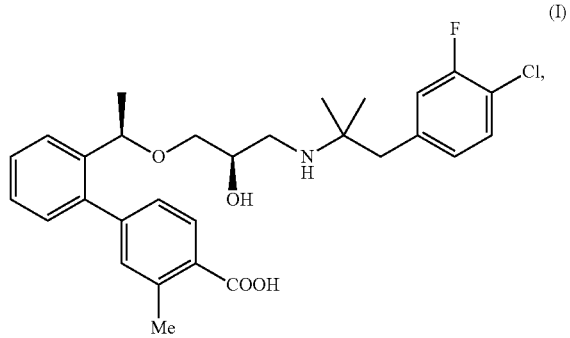 [SMILES: Cc1cc(-c2ccccc2[C@@H](C)OC[C@H](O)CNC(C)(C)Cc2ccc(Cl)c(F)c2)ccc1C(=O)O]

(I)

a solvate, a hydrate, a pharmaceutically acceptable salt, or a combination thereof; and
b) one or more pharmaceutically acceptable excipients selected from one or more fillers, one or more glidants, one or more disintegrants, one or more surfactants, one or more binders, one or more lubricants, and a combination thereof, wherein the compound is present in an amount of at least about 12% by weight, on a salt-free and anhydrous basis.

In some embodiments, the present disclosure provides a tablet formulation as a common blend formulation across a variety of dosage strengths. The common blend tablet formulation includes:
a) a compound represented by formula (I):

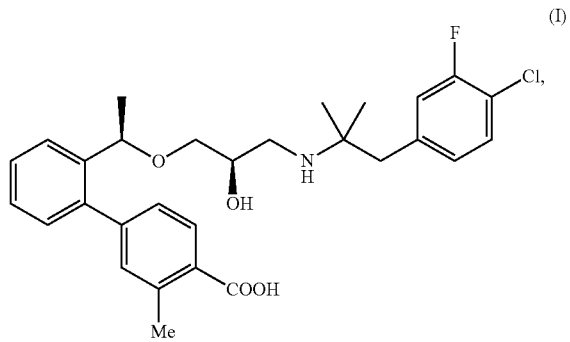 [SMILES: Cc1cc(-c2ccccc2[C@@H](C)OC[C@H](O)CNC(C)(C)Cc2ccc(Cl)c(F)c2)ccc1C(=O)O]

(I)

a solvate, a hydrate, a pharmaceutically acceptable salt, or a combination thereof; and
b) one or more pharmaceutically acceptable excipients selected from one or more fillers, one or more glidants, one or more disintegrants, one or more surfactants, one or more binders, one or more lubricants, and a combination thereof, wherein the compound is present in an amount of at least about 12% by weight, on a salt-free and anhydrous basis; and a ratio of the compound by weight to a total weight of one or more pharmaceutically acceptable excipients is constant across the two or more dosage strengths.

The compound of formula (I) can be in a pharmaceutically acceptable salt form, in a zwitterionic form, or in a neutral form, any of which is optionally in a solvate or hydrate form.

In some embodiments, a pharmaceutically acceptable acid addition salt of the compound of formula (I) is represented by formula (Ia):

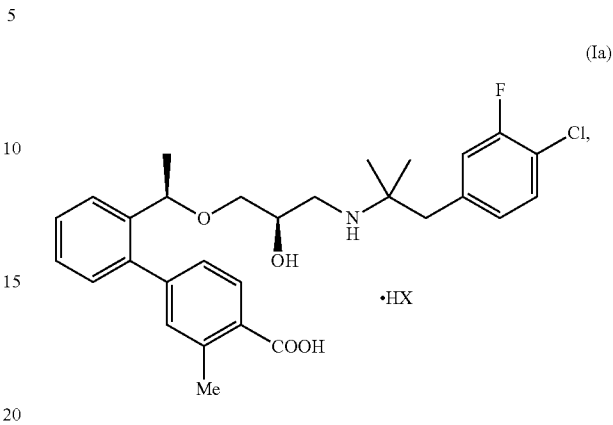

(Ia)

wherein HX is a pharmaceutically acceptable acid addition.

Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. In some embodiments, the compound of formula (I) is in a sulfate salt form. In some embodiments, the compound of formula (I) is in a hemisulfate salt form.

In some embodiments, a pharmaceutically acceptable base addition salt of the compound of formula (I) is represented by formula (Ib):

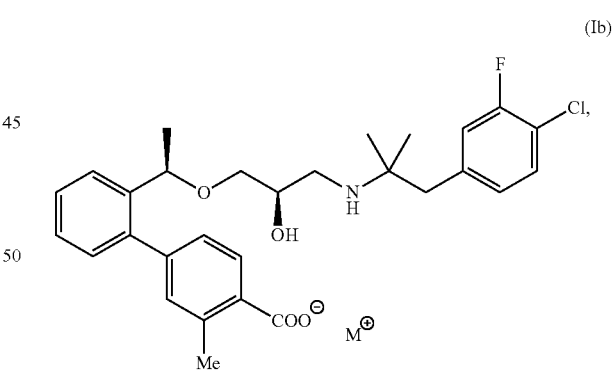

(Ib)

wherein M is a pharmaceutically acceptable cation of a base.

The base addition salts can be obtained by contacting the neutral form of the compound of formula (I) with a sufficient amount of the desired base, either neat or in a suitable inert solvent. Examples of pharmaceutically acceptable base addition salts include sodium, potassium, calcium, ammonium, organic amino, or magnesium salt, or a similar salt. In some embodiments, the compound of formula (I) is a sodium salt thereof.

In some embodiments, the compound of formula (I) is in a zwitterionic form having formula (Ic):

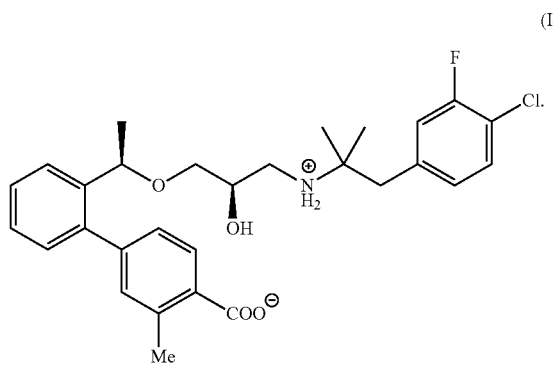

(Ic)

In some embodiments, the compound of formula (I) is in a neutral form.

In some embodiments, the compound of any one of formulae (I), (Ia), (Ib), and (Ic) is in a solvate and/or a hydrate form. In some embodiments, the compound of any one of formulae (I), (Ia), (Ib), and (Ic) is in a hydrate form.

In some embodiments, the compound of formula (I) is in a hemihydrate hemisulfate salt form as CLTX-305 represented by the formula:

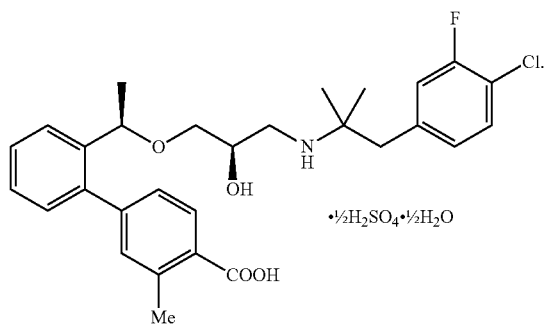 [SMILES: Cc1cc(-c2ccccc2[C@@H](C)OC[C@H](O)CNC(C)(C)Cc2ccc(Cl)c(F)c2)ccc1C(=O)O]

A tablet formulation provided herein can be in one or more dosage strengths, where the compound of formula (I) (e.g., CLTX-305) is present in an amount of at least about 1 milligram (mg), about 5 mg, about 10 mg, about 20 mg, about 50 mg, about 100 mg, about 200 mg, about 300 mg, about 400 mg, about 500 mg, or greater on a salt-free and anhydrous basis. In some embodiments, the compound of formula (I) (e.g., CLTX-305) is present in an amount of from about 1 to about 1000 mg, from about 1 to about 750 mg, from about 1 to about 500 mg, from about 1 to about 250 mg, from about 50 to about 1000 mg, from about 50 to about 750 mg, from about 50 to about 500 mg, from about 50 to about 250 mg, from about 100 to about 1000 mg, from about 100 to about 750 mg, from about 100 to about 500 mg, from about 100 to about 250 mg, from about 200 to about 1000 mg, from about 200 to about 750 mg, from about 200 to about 500 mg, from about 300 to about 1000 mg, from about 300 to about 750 mg, from about 300 to about 500 mg, from about 400 to about 1000 mg, from about 400 to about 750 mg, from about 500 to about 1000 mg, from about 500 to about 750 mg, from about 600 to about 1000 mg, from about 5 to about 250 mg, or from about 5 to about 100 mg, or any suitable range therein, in each tablet, on a salt-free and anhydrous basis. In some embodiments, the tablet formulation is in two or more different dosage strengths. In some embodiments, the compound of formula (I) (e.g., CLTX-305) is present in an amount of about 5 mg, about 10 mg, about 30 mg, about 60 mg, about 100 mg, about 150 mg, about 200 mg, about 250 mg, about 300 mg, about 400 mg, about 500 mg, about 600 mg, about 700 mg, about 800 mg, about 900 mg, or about 1000 mg in each tablet, on a salt-free and anhydrous basis. In some embodiments, the compound (e.g., CLTX-305) is present in an amount of about 5 mg, about 10 mg, about 30 mg, about 60 mg, about 100 mg, about 150 mg, about 200 mg, about 300 mg, about 400 mg, about 500 mg, or about 700 mg in each tablet, on a salt-free and anhydrous basis.

A tablet formulation provided herein can be in one or more dosage strengths, where CLTX-305 is present in an amount of at least about 1 mg, about 5 mg, about 10 mg, about 20 mg, about 50 mg, about 100 mg, about 200 mg, about 300 mg, about 400 mg, about 500 mg, or greater. In some embodiments, CLTX-305 is present in an amount from about 1 to about 1000 mg, from about 1 to about 750 mg, from about 1 to about 500 mg, from about 1 to about 250 mg, from about 50 to about 1000 mg, from about 50 to about 750 mg, from about 50 to about 500 mg, from about 50 to about 250 mg, from about 100 to about 1000 mg, from about 100 to about 750 mg, from about 100 to about 500 mg, from about 100 to about 250 mg, from about 200 to about 1000 mg, from about 200 to about 750 mg, from about 200 to about 500 mg, from about 300 to about 1000 mg, from about 300 to about 750 mg, from about 300 to about 500 mg, from about 400 to about 1000 mg, from about 400 to about 750 mg, from about 500 to about 1000 mg, from about 500 to about 750 mg, from about 600 to about 1000 mg, from about 5 to about 250 mg, or from about 5 to about 100 mg, or any suitable range therein, in each tablet. In some embodiments, the tablet formulation is in two or more different dosage strengths. In some embodiments, CLTX-305 is present in an amount of about 5 mg, about 10 mg, about 30 mg, about 60 mg, about 120 mg, about 180 mg, about 240 mg, about 300 mg, about 360 mg, about 420 mg, about 480 mg, about 540 mg, about 600 mg, about 660 mg, or about 720 mg in each tablet. In some embodiments, CLTX-305 is present in an amount of about 5 mg, about 10 mg, about 30 mg, about 60 mg, about 120 mg, about 240 mg, about 360 mg, or about 720 mg in each tablet.

The tablet formulation of the present disclosure can be a common blend formulation, where a ratio of the compound by weight to a total weight of one or more pharmaceutically acceptable excipients is constant across multiple dosage strengths. In some embodiments, a ratio of the compound by weight to a total weight of one or more pharmaceutically acceptable excipients is constant across two or more dosage strengths. In some embodiments, a ratio of the compound (e.g., CLTX-305) by weight to a total weight of one or more pharmaceutically acceptable excipients is constant across two or more dosage strengths, wherein the compound of formula (I) (e.g., CLTX-305) is present in an amount of about 5 mg, about 10 mg, about 30 mg, about 60 mg, about 100 mg, about 150 mg, about 200 mg, about 300 mg, about 400 mg, about 500 mg, or about 700 mg in each tablet, on a salt-free and anhydrous basis. In some embodiments, a ratio of the compound (e.g., CLTX-305) by weight to a total weight of one or more pharmaceutically acceptable excipients is constant across the two or more dosage strengths, wherein the compound is present in an amount of about 5 mg, about 10 mg, about 30 mg, about 60 mg, about 120 mg, about 240 mg, about 360 mg, or about 720 mg in each tablet.

In some embodiments, the weight/weight ratio of the compound of formula (I) (e.g., CLTX-305) to one or more pharmaceutically acceptable excipients combined is at least about 1:5, such as at least about 1:5, about 1:6, about 1:7, or greater, such as at least about 1:7.4, where the compound is on a salt-free and anhydrous basis. In some embodiments, the weight/weight ratio of the compound of formula (I) (e.g., CLTX-305) to one or more pharmaceutically acceptable excipients combined is from about 1:7.4 to about 1:2, where the compound is on a salt-free and anhydrous basis. In some embodiments, the weight/weight ratio of the compound (e.g., CLTX-305) to one or more pharmaceutically acceptable excipients combined is about 1:7, where the compound is on a salt-free and anhydrous basis. In some embodiments, the weight/weight ratio of the compound (e.g., CLTX-305) to one or more pharmaceutically acceptable excipients combined is about 1:7 across two or more dosage strengths, wherein the compound of formula (I) is present in an amount of about 10 mg, about 30 mg, about 60 mg, about 100 mg, about 150 mg, about 200 mg, about 300 mg, about 400 mg, about 500 mg, or about 700 mg in each tablet, on a salt-free and anhydrous basis.

In some embodiments, the weight/weight ratio of CLTX-305 to one or more pharmaceutically acceptable excipients combined is at least about 1:6.5. In some embodiments, the weight/weight ratio of CLTX-305 to one or more pharmaceutically acceptable excipients combined is from about 1:6.5 to about 1:2, such as about 1:3. In some embodiments, the weight/weight ratio of CLTX-305 to one or more pharmaceutically acceptable excipients combined is about 1:6. In some embodiments, the weight/weight ratio of CLTX-305 to one or more pharmaceutically acceptable excipients combined is about 1:6 across the two or more dosage strengths, wherein CLTX-305 is present in an amount of about 10 mg, about 30 mg, about 60 mg, about 120 mg, about 240 mg, about 360 mg, or about 720 mg in each tablet.

In some embodiments, the total weight (e.g., active ingredients plus excipients—not including coating) of a solid dosage form (e.g., tablet) is from about 30 to about 3000 mg. In some embodiments, the total weight of a solid dosage form (e.g., tablet) is about 70 mg, 210 mg, 420 mg, 700 mg, 1050 mg, 1400 mg, or 1750 mg. In some embodiments, the total weight of a solid dosage form (e.g., tablet) is about 70 mg, 210 mg, or 420 mg.

In some embodiments, the compound of formula (I) (e.g., CLTX-305) is present in an amount of at least about 12% by weight of the tablet formulation, on a salt-free and anhydrous basis. In some embodiments, the compound of formula (I) (e.g., CLTX-305) is present in an amount of from about 12% to about 32% by weight of the tablet formulation, on a salt-free and anhydrous basis. In some embodiments, the compound of formula (I) (e.g., CLTX-305) is present in an amount of from about 12% to about 30%, from about 12% to about 25%, from about 12% to about 20%, or from about 12% to about 15% by weight of the tablet formulation, on a salt-free and anhydrous basis. In some embodiments, the compound of formula (I) (e.g., CLTX-305) is present in an amount of from about 12% to about 15% by weight of the tablet formulation, on a salt-free and anhydrous basis. In some embodiments, the compound of formula (I) (e.g., CLTX-305) is present in an amount of about 13% by weight of the tablet formulation, on a salt-free and anhydrous basis.

In some embodiments, CLTX-305 is present in an amount of at least about 13% by weight of the tablet formulation. In some embodiments, CLTX-305 is present in an amount of from about 13% to about 35% by weight of the tablet formulation. In some embodiments, CLTX-305 is present in an amount of from about 13% to about 30%, from about 13% to about 25%, from about 13% to about 20%, or from about 13% to about 15% by weight of the tablet formulation. In some embodiments, CLTX-305 is present in an amount of from about 13% to about 15% by weight of the tablet formulation. In some embodiments, CLTX-305 is present in an amount of about 14.3% by weight of the tablet formulation.

In some embodiments, the tablet formulation includes at least two (2) pharmaceutically acceptable excipients selected from one or more fillers, one or more glidants, one or more disintegrants, one or more surfactants, one or more binders, one or more lubricants, and a combination thereof. In some embodiments, the tablet formulation includes at least three (3) pharmaceutically acceptable excipients selected from one or more fillers, one or more glidants, one or more disintegrants, one or more surfactants, one or more binders, one or more lubricants, and a combination thereof. In some embodiments, the tablet formulation includes at least four (4) pharmaceutically acceptable excipients selected from one or more fillers, one or more glidants, one or more disintegrants, one or more surfactants, one or more binders, one or more lubricants, and a combination thereof. In some embodiments, the tablet formulation includes at least five (5) pharmaceutically acceptable excipients selected from one or more fillers, one or more glidants, one or more disintegrants, one or more surfactants, one or more binders, one or more lubricants, and a combination thereof. In some embodiments, the tablet formulation includes at least six (6) pharmaceutically acceptable excipients selected from one or more fillers, one or more glidants, one or more disintegrants, one or more surfactants, one or more binders, one or more lubricants, and a combination thereof. In some embodiments, the tablet formulation includes seven (7) pharmaceutically acceptable excipients selected from one or more fillers, one or more glidants, one or more disintegrants, one or more surfactants, one or more binders, one or more lubricants, and a combination thereof. In some embodiments, the tablet formulation includes eight (8) pharmaceutically acceptable excipients selected from one or more fillers, one or more glidants, one or more disintegrants, one or more surfactants, one or more binders, one or more lubricants, and a combination thereof. In some embodiments, the tablet formulation includes two fillers (i.e., a first filler and a second filler), one glidant, one disintegrant, one surfactant, one binder, and one lubricant.

In some embodiments, the tablet formulation includes one or more fillers. In some embodiments, the tablet formulation includes two or more fillers. Suitable fillers are described herein. In some embodiments, the one or more fillers are present in an amount of from about 15% to about 70%, from about 20% to about 70%, from about 30% to about 70%, from about 40% to about 70%, from about 50% to about 70%, from about 40% to about 60%, or from about 50% to about 60% by weight of the tablet formulation. In some embodiments, the one or more fillers are present in an amount of from about 40% to about 70%, from about 50% to about 70%, from about 40% to about 60%, or from about 50% to about 60% by weight of the tablet formulation. In some embodiments, the one or more fillers are present in an amount of from about 50% to about 60% by weight of the tablet formulation. In some embodiments, one or more fillers are present in an amount of about 55.2% by weight.

In some embodiments, the tablet formulation includes one to three fillers. In some embodiments, the tablet formulation includes one to two fillers. In some embodiments, the tablet formulation includes two to three fillers. In some embodiments, the tablet formulation includes two fillers (i.e., a first filler and a second filler).

Suitable fillers include, for example, oligosaccharides (e.g., lactose), sugars, starches, modified starches, sugar alcohols (e.g. mannitol, sorbitol, xylitol, lactitol), inorganic salts, cellulose derivatives (e.g. microcrystalline cellulose, silicified microcrystalline cellulose, cellulose, calcium sulfate, aluminum and magnesium silicate complexes and oxides, and the like. Example of inorganic salt fillers include a phosphate salt, such as dibasic calcium phosphate, and salts of sulfates. In some embodiments, the one or more fillers include sugars, sugar alcohols, cellulose derivatives, or a combination thereof. In some embodiments, the one or more fillers include sugar alcohols, cellulose derivatives, or a combination thereof. In some embodiments, the one or more fillers are mannitol, sorbitol, xylitol, lactitol, microcrystalline cellulose, silicified microcrystalline cellulose, cellulose, or a combination thereof. In some embodiments, the one or more fillers include mannitol and microcrystalline cellulose. In some embodiments, the first filler includes sugar alcohols; and the second filler includes cellulose derivatives. In some embodiments, the first filler is mannitol; and the second filler is microcrystalline cellulose. In some embodiments, the first filler is mannitol; and the second filler is microcrystalline cellulose, wherein a ratio of mannitol to microcrystalline cellulose is no more than 5. In some embodiments, the first filler is mannitol; and the second filler is microcrystalline cellulose, wherein a ratio of mannitol to microcrystalline cellulose is no more than 3. In some embodiments, the first filler is mannitol; and the second filler is microcrystalline cellulose, wherein a ratio of mannitol to microcrystalline cellulose is about 2.5.

In some embodiments, mannitol and microcrystalline cellulose are present in an amount of from about 15% to about 70%, from about 20% to about 70%, from about 30% to about 70%, from about 40% to about 70%, from about 40% to about 60%, from about 50% to about 70%, or from about 50% to about 60% by weight of the tablet formulation. In some embodiments, mannitol and microcrystalline cellulose are present in an amount of from about 40% to about 70%, from about 40% to about 60%, from about 50% to about 70%, or from about 50% to about 60% by weight of the tablet formulation. In some embodiments, mannitol and microcrystalline cellulose are present in an amount of from about 50% to about 60% by weight of the tablet formulation. In some embodiments, mannitol and microcrystalline cellulose are present in an amount of about 55.2% by weight of the tablet formulation. In some embodiments, mannitol and microcrystalline cellulose are present in an amount of about 55.2% by weight of the tablet formulation, wherein a ratio of mannitol to microcrystalline cellulose is no more than about 3.0. In some embodiments, mannitol and microcrystalline cellulose are present in an amount of about 55.2% by weight of the tablet formulation, wherein a ratio of mannitol to microcrystalline cellulose is about 2.5. In some embodiments, mannitol is present in an amount of from about 10% to about 60%, from about 20% to about 60%, from about 30% to about 60%, or from about 30% to about 50% by weight of the tablet formulation. In some embodiments, mannitol is present in an amount of from about 30% to about 50% by weight of the tablet formulation. In some embodiments, mannitol is present in an amount of about 39.5% by weight of the tablet formulation. In some embodiments, microcrystalline cellulose is present in an amount of from about 10% to about 25%, or from about 10% to about 20% by weight of the tablet formulation. In some embodiments, microcrystalline cellulose is present in an amount of from about 10% to about 20% by weight of the tablet formulation. In some embodiments, microcrystalline cellulose is present in an amount of about 15.7% by weight of the tablet formulation.

In some embodiments, the tablet formulation includes one or more glidants. Suitable glidants are described below. In some embodiments, the one or more glidants are present in an amount of from about 0.1% to about 5%, from about 0.5% to about 5%, from about 1% to about 5%, from about 1% to about 4%, or from about 2% to about 4% by weight of the tablet formulation. In some embodiments, the one or more glidants are present in an amount of from about 1% to about 5%, from about 1% to about 4%, or from about 2% to about 4% by weight of the tablet formulation. In some embodiments, the one or more glidants are present in an amount of from about 2% to about 4% by weight of the tablet formulation. In some embodiments, the one or more glidants are present in an amount of about 3.0% by weight of the tablet formulation.

In some embodiments, the tablet formulation includes one or two glidants. In some embodiments, the tablet formulation includes one glidant.

Suitable glidants include, for example, magnesium carbonate, fumed silica (colloidal silicon dioxide), and talc. In some embodiments, the one or more glidants are silicon dioxide, talc, magnesium carbonate, or a combination thereof. In some embodiments, the one or more glidants include colloidal silicon dioxide. In some embodiments, the tablet formulation includes one glidant; and the one glidant is colloidal silicon dioxide.

In some embodiments, colloidal silicon dioxide is present in an amount of from about 0.1% to about 5%, from about 0.5% to about 5%, from about 1% to about 5%, from about 1% to about 4%, or from about 2% to about 4% by weight of the tablet formulation. In some embodiments, colloidal silicon dioxide is present in an amount of from about 1% to about 5%, from about 1% to about 4%, or from about 2% to about 4% by weight of the tablet formulation.

In some embodiments, colloidal silicon dioxide is present in an amount of from about 2% to about 4% by weight of the tablet formulation. In some embodiments, colloidal silicon dioxide is present in an amount of about 3.0% by weight of the tablet formulation.

In some embodiments, the tablet formulation includes one or more disintegrants. Suitable disintegrants are described below. In some embodiments, the one or more disintegrants are present in an amount of from about 1% to about 30%, from about 5% to about 30%, from about 10% to about 30%, from about 15% to about 30%, or from about 15% to about 25% by weight of the tablet formulation. In some embodiments, the one or more disintegrants are present in an amount of from about 10% to about 30%, from about 15% to about 30%, or from about 15% to about 25% by weight of the tablet formulation. In some embodiments, the one or more disintegrants are present in an amount of from about 15% to about 25% by weight of the tablet formulation. In some embodiments, the one or more disintegrants are present in an amount of about 20.0% by weight of the tablet formulation.

When wet granulation is used, in some embodiments, a portion of the one or more disintegrants is added during granulation so that the disintegrants remain within the granules (i.e., intragranular); and the remaining portion of the one or more disintegrants is added to the final blend so that the disintegrants reside outside the granules (i.e., extragranular). In some embodiments, the one or more disintegrants are present intragranularly, extragranularly, or a combination thereof. In some embodiments, the one or more disintegrants are present both intragranularly and extragranularly. In some embodiments, the one or more disintegrants are present intragranularly in an amount of from about 1% to about 15% by weight of the tablet formulation. In some embodiments, the one or more disintegrants are present intragranularly in an amount of about 10.0% by weight of the tablet formulation. In some embodiments, the one or more disintegrants are present extragranularly in an amount of from about 1% to about 15% by weight of the tablet formulation. In some embodiments, the one or more disintegrants are present extragranularly in an amount of about 10.0% by weight of the tablet formulation.

In some embodiments, the tablet formulation includes one to two disintegrants. In some embodiments, the tablet formulation includes one disintegrant.

Suitable disintegrants include, for example, croscarmellose sodium, crospovidone, sodium starch glycolate, and corn starch. In some embodiments, the one or more disintegrants include croscarmellose sodium. In some embodiments, the tablet formulation includes one disintegrant; and the one disintegrant is croscarmellose sodium.

In some embodiments, croscarmellose sodium is present in an amount of from about 1% to about 30%, from about 5% to about 30%, from about 10% to about 30%, from about 15% to about 30%, or from about 15% to about 25% by weight of the tablet formulation. In some embodiments, croscarmellose sodium is present in an amount of from about 10% to about 30%, from about 15% to about 30%, or from about 15% to about 25% by weight of the tablet formulation. In some embodiments, croscarmellose sodium is present in an amount of from about 15% to about 25% by weight of the tablet formulation. In some embodiments, croscarmellose sodium is present in an amount of about 20.0% by weight of the tablet formulation. In some embodiments, croscarmellose sodium is present intragranularly, extragranularly, or a combination thereof. In some embodiments, croscarmellose sodium is present both intragranularly and extragranularly. In some embodiments, croscarmellose sodium is present intragranularly in an amount of from about 1% to about 15% by weight of the tablet formulation. In some embodiments, croscarmellose sodium is present intragranularly in an amount of about 10.0% by weight of the tablet formulation. In some embodiments, croscarmellose sodium is present extragranularly in an amount of from about 1% to about 15% by weight of the tablet formulation. In some embodiments, croscarmellose sodium is present extragranularly in an amount of about 10.0% by weight of the tablet formulation.

In some embodiments, the tablet formulation includes one or more surfactants. Suitable surfactants are described below. In some embodiments, the one or more surfactants are present in an amount of from about 0.5% to about 5%, from about 1% to about 5%, from about 1% to about 4%, or from about 1% to about 3% by weight of the tablet formulation. In some embodiments, the one or more surfactants are present in an amount of from about 1% to about 5%, from about 1% to about 4%, or from about 1% to about 3% by weight of the tablet formulation. In some embodiments, the one or more surfactants are present in an amount of from about 1% to about 3% by weight of the tablet formulation. In some embodiments, the one or more surfactants are present in an amount of about 2.0% by weight of the tablet formulation.

In some embodiments, the tablet formulation includes one or two surfactants. In some embodiments, the tablet formulation includes one surfactant.

Surfactants useful in the present disclosure include, but are not limited to, a non-ionic surfactant, a cationic surfactant, an anionic surfactant, an amphoteric surfactant, an ampholytic surfactant, a fatty alcohol, a fatty acid, and a salt of a fatty acid. In some embodiments, the one or more surfactants include non-ionic surfactants. Suitable non-ionic surfactants include polyol esters (sucrose, glycol, glycerol, and sorbitan fatty acid esters), polyoxyethylene esters, and poloxamers. In some embodiments, the one or more surfactants include polyol fatty acid esters. In some embodiments, the one or more surfactants are a sucrose fatty acid ester, a glycol fatty acid ester, a glycerol fatty acid ester, a sorbitan fatty acid ester, or a combination thereof. In some embodiments, the one or more surfactants are one or more sucrose fatty acid esters. In some embodiments, the one or more surfactants are one or more sucrose fatty acid esters including sucrose palmitate. In some embodiments, the tablet formulation includes one surfactant; and the one surfactant is one or more sucrose fatty acid esters including sucrose palmitate.

In some embodiments, the one or more sucrose fatty acid esters are present in an amount of from about 0.5% to about 5%, from about 1% to about 5%, from about 1% to about 4%, or from about 1% to about 3% by weight of the tablet formulation. In some embodiments, the one or more sucrose fatty acid esters are present in an amount of from about 1% to about 3% by weight of the tablet formulation. In some embodiments, the one or more sucrose fatty acid esters are present in an amount of about 2.0% by weight of the tablet formulation.

In some embodiments, the tablet formulation includes one or more binders. Suitable binders are described below. In some embodiments, the one or more binders are present in an amount of from about 1% to about 5%, from about 2% to about 5%, or from about 3% to about 5% by weight of the tablet formulation. In some embodiments, the one or more binders are present in an amount of from about 3% to about 5% by weight of the tablet formulation. In some embodiments, the one or more binders are present in an amount of about 4.0% by weight of the tablet formulation.

In some embodiments, the tablet formulation includes one to two binders. In some embodiments, the tablet formulation includes one binder.

Suitable binders include, for example, povidone, lactose, starches, modified starches, sugars, gum acacia, gum tragacanth, guar gum, pectin, wax binders, methylcellulose, carboxymethylcellulose, hydroxypropyl methylcellulose, hydroxyethyl cellulose, hydroxypropyl cellulose, copovidone, gelatin, sodium alginate, and the like. In some embodiments, the one or more binders are cellulosic binders. In some embodiments, the one or more binders are methylcellulose, carboxymethylcellulose, hydroxypropyl methylcellulose, hydroxyethyl cellulose, hydroxypropyl cellulose, or a combination thereof. In some embodiments, the one or more binders include hydroxypropyl methylcellulose. In some embodiments, the tablet formulation includes one binder; and the one binder is hydroxypropyl methylcellulose.

In some embodiments, hydroxypropyl methylcellulose is present in an amount of from about 1% to about 5%, from about 2% to about 5%, or from about 3% to about 5% by weight of the tablet formulation. In some embodiments, hydroxypropyl methylcellulose is present in an amount of from about 3% to about 5% by weight of the tablet formulation. In some embodiments, hydroxypropyl methylcellulose is present in an amount of about 4.0% by weight of the tablet formulation.

In some embodiments, the tablet formulation includes one or more lubricants. Suitable lubricants are described below. In some embodiments, the one or more lubricants are present in an amount of from about 0.2% to about 5%, from about 1% to about 5%, from about 1% to about 4%, from about 1% to about 3% or from about 1% to about 2% by weight of the tablet formulation. In some embodiments, the one or more lubricants are present in an amount of from about 1% to about 3% or from about 1% to about 2% by weight of the tablet formulation. In some embodiments, the one or more lubricants are present in an amount of from about 1% to about 2% by weight of the tablet formulation. In some embodiments, the one or more lubricants are present in an amount of about 1.5% by weight of the tablet formulation.

In some embodiments, the tablet formulation includes one to two lubricants. In some embodiments, the tablet formulation includes one lubricant.

Suitable lubricants include, for example, magnesium stearate, calcium stearate, zinc stearate, sodium stearyl fumarate, ethyl oleate, ethyl laureate, stearic acid, palmitic acid, sodium lauryl sulfate, talc, carnauba wax, hydrogenated vegetable oils, mineral oil, and polyethylene glycols. In some embodiments, the one or more lubricants are magnesium stearate, calcium stearate, zinc stearate, sodium stearyl fumarate, ethyl oleate, ethyl laureate, stearic acid, palmitic acid, sodium lauryl sulfate, or a combination thereof. In some embodiments, the one or more lubricants are magnesium stearate, calcium stearate, zinc stearate, sodium stearyl fumarate, stearic acid, sodium lauryl sulfate, or a combination thereof. In some embodiments, the one or more lubricants are magnesium stearate, calcium stearate, zinc stearate, sodium stearyl fumarate, or a combination thereof. In some embodiments, the one or more lubricants include magnesium stearate. In some embodiments, the tablet formulation includes one lubricant; and the one lubricant is magnesium stearate.

In some embodiments, magnesium stearate is present in an amount of from about 0.2% to about 5%, from about 1% to about 5%, from about 1% to about 4%, from about 1% to about 3% or from about 1% to about 2% by weight of the tablet formulation. In some embodiments, magnesium stearate is present in an amount of from about 1% to about 3% or from about 1% to about 2% by weight of the tablet formulation. In some embodiments, magnesium stearate is present in an amount of from about 1% to about 2% by weight of the tablet formulation. In some embodiments, magnesium stearate is present in an amount of about 1.5% by weight of the tablet formulation.

In some embodiments, the one or more lubricants are present in the tablet formulation.

In some embodiments, magnesium stearate is present in the tablet formulation. In some embodiments, magnesium stearate is present in an amount of from about 1 to about 2% by weight of the tablet formulation. In some embodiments, magnesium stearate is present in an amount of about 1.5% by weight of the tablet formulation.

Other suitable fillers, glidants, disintegrants, surfactants, binders, lubricants and other excipients which may be used are described in Handbook of Pharmaceutical Excipients, 5th Edition, 2006, American Lachman, Leon; Pharmaceutical Dosage Forms: Tablets Volume 1, 3rd Edition, 2008, Lieberman, Herbert A., et al; Modern Pharmaceutics, 4th Edition, 2002, Banker, Gilbert and Rhodes, Christopher T; and Remington's Pharmaceutical Sciences, 23rd Edition, 2020, each of which is incorporated herein by reference in its entirety.

In some embodiments, the tablet formulation includes:
a) from about 13% to about 35% by weight of CLTX-305; and
b) two or more pharmaceutically acceptable excipients selected from the group consisting of a first filler, a second filler, a glidant, a disintegrant, a surfactant, a binder, and a lubricant,
wherein:
the first filler is mannitol, sorbitol, xylitol, lactitol, or a combination thereof;
the second filler is microcrystalline cellulose, silicified microcrystalline cellulose, cellulose, or a combination thereof;
the glidant is silicon dioxide, talc, magnesium carbonate, or a combination thereof;
the disintegrant is croscarmellose sodium, crospovidone, sodium starch glycolate, corn starch, or a combination thereof;
the surfactant is one or more sucrose fatty acid esters, one or more glycol fatty acid esters, one or more glycerol fatty acid esters, one or more sorbitan fatty acid esters, or a combination thereof;
the binder is methylcellulose, hydroxypropyl methylcellulose, hydroxyethyl cellulose, hydroxypropyl cellulose, or a combination thereof; and
the lubricant is magnesium stearate, calcium stearate, zinc stearate, sodium stearyl fumarate, or a combination thereof.

In some embodiments, the tablet formulation includes:
a) from about 13% to about 35% by weight of CLTX-305; and
b) three or more pharmaceutically acceptable excipients selected from the group consisting of a first filler, a second filler, a glidant, a disintegrant, a surfactant, a binder, and a lubricant,
wherein:
the first filler is mannitol, sorbitol, xylitol, lactitol, or a combination thereof;
the second filler is microcrystalline cellulose, silicified microcrystalline cellulose, cellulose, or a combination thereof;
the glidant is silicon dioxide, talc, magnesium carbonate, or a combination thereof;
the disintegrant is croscarmellose sodium, crospovidone, sodium starch glycolate, corn starch, or a combination thereof;
the surfactant is one or more sucrose fatty acid esters, one or more glycol fatty acid esters, one or more glycerol fatty acid esters, one or more sorbitan fatty acid esters, or a combination thereof;
the binder is methylcellulose, hydroxypropyl methylcellulose, hydroxyethyl cellulose, hydroxypropyl cellulose, or a combination thereof; and
the lubricant is magnesium stearate, calcium stearate, zinc stearate, sodium stearyl fumarate, or a combination thereof.

In some embodiments, the tablet formulation includes:
a) from about 13% to about 35% by weight of CLTX-305; and
b) four or more pharmaceutically acceptable excipients selected from the group consisting of a first filler, a second filler, a glidant, a disintegrant, a surfactant, a binder, and a lubricant, wherein:
   the first filler is mannitol, sorbitol, xylitol, lactitol, or a combination thereof;
   the second filler is microcrystalline cellulose, silicified microcrystalline cellulose, cellulose, or a combination thereof;
   the glidant is silicon dioxide, talc, magnesium carbonate, or a combination thereof;
   the disintegrant is croscarmellose sodium, crospovidone, sodium starch glycolate, corn starch, or a combination thereof;
   the surfactant is one or more sucrose fatty acid esters, one or more glycol fatty acid esters, one or more glycerol fatty acid esters, one or more sorbitan fatty acid esters, or a combination thereof;
   the binder is methylcellulose, hydroxypropyl methylcellulose, hydroxyethyl cellulose, hydroxypropyl cellulose, or a combination thereof; and
   the lubricant is magnesium stearate, calcium stearate, zinc stearate, sodium stearyl fumarate, or a combination thereof.

In some embodiments, the tablet formulation includes:
a) from about 13% to about 35% by weight of CLTX-305; and
b) five or more pharmaceutically acceptable excipients selected from the group consisting of a first filler, a second filler, a glidant, a disintegrant, a surfactant, a binder, and a lubricant,
wherein:
   the first filler is mannitol, sorbitol, xylitol, lactitol, or a combination thereof;
   the second filler is microcrystalline cellulose, silicified microcrystalline cellulose, cellulose, or a combination thereof;
   the glidant is silicon dioxide, talc, magnesium carbonate, or a combination thereof;
   the disintegrant is croscarmellose sodium, crospovidone, sodium starch glycolate, corn starch, or a combination thereof;
   the surfactant is one or more sucrose fatty acid esters, one or more glycol fatty acid esters, one or more glycerol fatty acid esters, one or more sorbitan fatty acid esters, or a combination thereof;
   the binder is methylcellulose, hydroxypropyl methylcellulose, hydroxyethyl cellulose, hydroxypropyl cellulose, or a combination thereof; and
   the lubricant is magnesium stearate, calcium stearate, zinc stearate, sodium stearyl fumarate, or a combination thereof.

In some embodiments, the tablet formulation includes:
a) from about 13% to about 35% by weight of CLTX-305; and
b) six or more pharmaceutically acceptable excipients selected from the group consisting of a first filler, a second filler, a glidant, a disintegrant, a surfactant, a binder, and a lubricant,
wherein:
   the first filler is mannitol, sorbitol, xylitol, lactitol, or a combination thereof;
   the second filler is microcrystalline cellulose, silicified microcrystalline cellulose, cellulose, or a combination thereof;
   the glidant is silicon dioxide, talc, magnesium carbonate, or a combination thereof;
   the disintegrant is croscarmellose sodium, crospovidone, sodium starch glycolate, corn starch, or a combination thereof;
   the surfactant is one or more sucrose fatty acid esters, one or more glycol fatty acid esters, one or more glycerol fatty acid esters, one or more sorbitan fatty acid esters, or a combination thereof;
   the binder is methylcellulose, hydroxypropyl methylcellulose, hydroxyethyl cellulose, hydroxypropyl cellulose, or a combination thereof; and
   the lubricant is magnesium stearate, calcium stearate, zinc stearate, sodium stearyl fumarate, or a combination thereof.

In some embodiments, the tablet formulation includes:
a) from about 13% to about 35% by weight of CLTX-305; and
b) seven or more pharmaceutically acceptable excipients including a first filler, a second filler, a glidant, a disintegrant, a surfactant, a binder, and a lubricant,
wherein:
   the first filler is mannitol, sorbitol, xylitol, lactitol, or a combination thereof;
   the second filler is microcrystalline cellulose, silicified microcrystalline cellulose, cellulose, or a combination thereof;
   the glidant is silicon dioxide, talc, magnesium carbonate, or a combination thereof;
   the disintegrant is croscarmellose sodium, crospovidone, sodium starch glycolate, corn starch, or a combination thereof;
   the surfactant is one or more sucrose fatty acid esters, one or more glycol fatty acid esters, one or more glycerol fatty acid esters, one or more sorbitan fatty acid esters, or a combination thereof;
   the binder is methylcellulose, hydroxypropyl methylcellulose, hydroxyethyl cellulose, hydroxypropyl cellulose, or a combination thereof; and
   the lubricant is magnesium stearate, calcium stearate, zinc stearate, sodium stearyl fumarate, or a combination thereof.

In some embodiments, the tablet formulation includes:
a) from about 13% to about 35% by weight of CLTX-305; and
b) two or more pharmaceutically acceptable excipients selected from the group consisting of a first filler, a second filler, a glidant, a disintegrant, a surfactant, a binder, and a lubricant,
wherein:
   the first filler is mannitol;
   the second filler is microcrystalline cellulose;
   the glidant is colloidal silicon dioxide;
   the disintegrant is croscarmellose sodium;
   the surfactant is one or more sucrose fatty acid esters including sucrose palmitate;
   the binder is hydroxypropyl methylcellulose; and
   the lubricant is magnesium stearate.

In some embodiments, the tablet formulation includes:
a) from about 13% to about 35% by weight of CLTX-305; and
b) three or more pharmaceutically acceptable excipients selected from the group consisting of a first filler, a second filler, a glidant, a disintegrant, a surfactant, a binder, and a lubricant,
wherein:
   the first filler is mannitol;
   the second filler is microcrystalline cellulose;
   the glidant is colloidal silicon dioxide;
   the disintegrant is croscarmellose sodium;
   the surfactant is one or more sucrose fatty acid esters including sucrose palmitate;

the binder is hydroxypropyl methylcellulose; and
the lubricant is magnesium stearate.

In some embodiments, the tablet formulation includes:
a) from about 13% to about 35% by weight of CLTX-305; and
b) four or more pharmaceutically acceptable excipients selected from the group consisting of a first filler, a second filler, a glidant, a disintegrant, a surfactant, a binder, and a lubricant, wherein:
the first filler is mannitol;
the second filler is microcrystalline cellulose;
the glidant is colloidal silicon dioxide;
the disintegrant is croscarmellose sodium;
the surfactant is one or more sucrose fatty acid esters including sucrose palmitate;
the binder is hydroxypropyl methylcellulose; and
the lubricant is magnesium stearate.

In some embodiments, the tablet formulation includes:
a) from about 13% to about 35% by weight of CLTX-305; and
b) five or more pharmaceutically acceptable excipients selected from the group consisting of a first filler, a second filler, a glidant, a disintegrant, a surfactant, a binder, and a lubricant, wherein:
the first filler is mannitol;
the second filler is microcrystalline cellulose;
the glidant is colloidal silicon dioxide;
the disintegrant is croscarmellose sodium;
the surfactant is one or more sucrose fatty acid esters including sucrose palmitate;
the binder is hydroxypropyl methylcellulose; and
the lubricant is magnesium stearate.

In some embodiments, the tablet formulation includes:
a) from about 13% to about 35% by weight of CLTX-305; and
b) six or more pharmaceutically acceptable excipients selected from the group consisting of a first filler, a second filler, a glidant, a disintegrant, a surfactant, a binder, and a lubricant, wherein:
the first filler is mannitol;
the second filler is microcrystalline cellulose;
the glidant is colloidal silicon dioxide;
the disintegrant is croscarmellose sodium;
the surfactant is one or more sucrose fatty acid esters including sucrose palmitate;
the binder is hydroxypropyl methylcellulose; and
the lubricant is magnesium stearate.

In some embodiments, the tablet formulation includes:
a) from about 13% to about 35% by weight of CLTX-305; and
b) seven or more pharmaceutically acceptable excipients including a first filler, a second filler, a glidant, a disintegrant, a surfactant, a binder, and a lubricant, wherein:
the first filler is mannitol;
the second filler is microcrystalline cellulose;
the glidant is colloidal silicon dioxide;
the disintegrant is croscarmellose sodium;
the surfactant is one or more sucrose fatty acid esters including sucrose palmitate;
the binder is hydroxypropyl methylcellulose; and
the lubricant is magnesium stearate.

In some embodiments, the tablet formulation includes:
a) from about 13% to about 15% by weight of CLTX-305;
b) from about 40% to about 70% by weight of a first filler and a second filler;
c) from about 1% to about 5% by weight of a glidant;
d) from about 10% to about 30% by weight of a disintegrant;
e) from about 1% to about 5% by weight of a surfactant;
f) from about 1% to about 5% by weight of a binder; and
g) from about 1% to about 3% by weight of a lubricant,
wherein the total weight of components from a) to g) is 100%.

In some embodiments, the tablet formulation includes:
a) from about 13% to about 15% by weight of CLTX-305;
b) from about 40% to about 70% by weight of a first filler and a second filler;
c) from about 1% to about 4% by weight of a glidant;
d) from about 15% to about 30% by weight of a disintegrant;
e) from about 1% to about 4% by weight of a surfactant;
f) from about 2% to about 5% by weight of a binder; and
g) from 1% to 3% by weight of a lubricant,
wherein the total weight of components from a) to g) is 100%.

In some embodiments, the tablet formulation includes:
a) from about 13% to about 15% by weight of CLTX-305;
b) from about 45% to about 65% by weight of a first filler and a second filler;
c) from about 2% to about 4% by weight of a glidant;
d) from about 15% to about 25% by weight of a disintegrant;
e) from about 1% to about 3% by weight of a surfactant;
f) from about 3% to about 5% by weight of a binder; and
g) from about 1% to about 2% by weight of a lubricant,
wherein the total weight of components from a) to g) is 100%.

In some embodiments, the tablet formulation includes:
a) from about 13% to about 15% by weight of CLTX-305;
b) from about 30% to about 60% by weight of a first filler;
c) from about 10% to about 30% by weight of a second filler;
d) from about 1% to about 5% by weight of a glidant;
e) from about 10% to about 30% by weight of a disintegrant;
f) from about 1% to about 5% by weight of a surfactant;
g) from about 1% to about 10% by weight of a binder; and
h) from about 1% to about 3% by weight of a lubricant,
wherein the total weight of components from a) to h) is 100%.

In some embodiments, the tablet formulation includes:
a) from about 13% to about 15% by weight of CLTX-305;
b) from about 30% to about 50% by weight of a first filler;
c) from about 10% to about 20% by weight of a second filler;
d) from about 2% to about 4% by weight of a glidant;
e) from about 15% to about 25% by weight of a disintegrant;
f) from about 1% to about 3% by weight of a surfactant;
g) from about 3% to about 5% by weight of a binder; and
h) from about 1% to about 2% by weight of a lubricant,
wherein the total weight of components from a) to h) is 100%.

In some embodiments, the tablet formulation includes:
a) from about 13% to about 15% by weight of CLTX-305;
b) from about 30% to about 50% by weight of a first filler;
c) from about 10% to about 20% by weight of a second filler;

d) from about 2% to about 4% by weight of a glidant;
e) from about 5% to about 15% by weight of an intragranular disintegrant;
f) from about 5% to about 15% by weight of an extragranular disintegrant;
g) from about 1% to about 3% by weight of a surfactant;
h) from about 3% to about 5% by weight of a binder; and
i) from about 1% to about 2% by weight of a lubricant, wherein the total weight of components from a) to i) is 100%.

In some embodiments, the tablet formulation includes:
a) from about 13% to about 15% by weight of CLTX-305;
b) from about 30% to about 50% by weight of a first filler selected from the group consisting of mannitol, sorbitol, xylitol, and lactitol;
c) from about 10% to about 20% by weight of a second filler selected from the group consisting of microcrystalline cellulose, silicified microcrystalline cellulose, and cellulose;
d) from about 2% to about 4% by weight of a glidant selected from the group consisting of silicon dioxide, talc, and magnesium carbonate;
e) from about 15% to about 25% by weight of a disintegrant selected from the group consisting of croscarmellose sodium, crospovidone, sodium starch glycolate, and corn starch;
f) from about 1% to about 3% by weight of a surfactant selected from the group consisting of sucrose fatty acid esters, glycol fatty acid esters, glycerol fatty acid esters, and sorbitan fatty acid esters;
g) from about 3% to about 5% by weight of a binder selected from the group consisting of methylcellulose, hydroxypropyl methylcellulose, hydroxyethyl cellulose, and hydroxypropyl cellulose; and
h) from about 1% to about 2% by weight of a lubricant selected from the group consisting of magnesium stearate, calcium stearate, zinc stearate, and sodium stearyl fumarate, wherein the total weight of components from a) to h) is 100%.

In some embodiments, the tablet formulation includes:
a) from about 13% to about 15% by weight of CLTX-305;
b) from about 30% to about 50% by weight of a first filler selected from the group consisting of mannitol, sorbitol, xylitol, and lactitol;
c) from about 10% to about 20% by weight of a second filler selected from the group consisting of microcrystalline cellulose, silicified microcrystalline cellulose, and cellulose;
d) from about 2% to about 4% by weight of a glidant selected from the group consisting of silicon dioxide, talc, and magnesium carbonate;
e) from about 5% to about 15% by weight of a first disintegrant selected from the group consisting of croscarmellose sodium, crospovidone, sodium starch glycolate, and corn starch, wherein the first disintegrant is present intragranularly;
f) from about 5% to about 15% by weight of a second disintegrant selected from the group consisting of croscarmellose sodium, crospovidone, sodium starch glycolate, and corn starch, wherein the second disintegrant is present extragranularly;
g) from about 1% to about 3% by weight of a surfactant selected from the group consisting of sucrose fatty acid esters, glycol fatty acid esters, glycerol fatty acid esters, and sorbitan fatty acid esters;
h) from about 3% to about 5% by weight of a binder selected from the group consisting of methylcellulose, hydroxypropyl methylcellulose, hydroxyethyl cellulose, and hydroxypropyl cellulose; and
i) from about 1% to about 2% by weight of a lubricant selected from the group consisting of magnesium stearate, calcium stearate, zinc stearate, and sodium stearyl fumarate, wherein the total weight of components from a) to i) is 100%.

In some embodiments, the tablet formulation includes:
a) from about 13% to about 15% by weight of CLTX-305;
b) from about 30% to about 50% by weight of mannitol;
c) from about 10% to about 20% by weight of microcrystalline cellulose;
d) from about 2% to about 4% by weight of colloidal silicon dioxide;
e) from about 15% to about 25% by weight of croscarmellose sodium;
f) from about 1% to about 3% by weight of one or more sucrose fatty acid esters including sucrose palmitate;
g) from about 3% to about 5% by weight of hydroxypropyl methylcellulose; and
h) from about 1% to about 2% by weight of magnesium stearate, wherein the total weight of components from a) to h) is 100%.

In some embodiments, the tablet formulation includes:
a) from about 13% to about 15% by weight of CLTX-305;
b) from about 30% to about 50% by weight of mannitol;
c) from about 10% to about 20% by weight of microcrystalline cellulose;
d) from about 2% to about 4% by weight of colloidal silicon dioxide;
e) from about 5% to about 15% by weight of croscarmellose sodium intragranularly;
f) from about 5% to about 15% by weight of croscarmellose sodium extragranularly;
g) from about 1% to about 3% by weight of one or more sucrose fatty acid esters including sucrose palmitate;
h) from about 3% to about 5% by weight of hydroxypropyl methylcellulose; and
i) from about 1% to about 2% by weight of magnesium stearate, wherein the total weight of components from a) to i) is 100%.

In some embodiments, the tablet formulation includes:
a) about 14.3% by weight of CLTX-305;
b) about 39.5% by weight of mannitol;
c) about 15.7% by weight of microcrystalline cellulose;
d) about 3.0% by weight of colloidal silicon dioxide;
e) about 2.0% by weight of croscarmellose sodium;
f) about 2.0% by weight of one or more sucrose fatty acid esters including sucrose palmitate;
g) about 4.0% by weight of hydroxypropyl methylcellulose; and
h) about 1.5% by weight of magnesium stearate, wherein the total weight of components from a) to h) is 100%.

In some embodiments, the tablet formulation includes:
a) about 14.3% by weight of CLTX-305;
b) about 39.5% by weight of mannitol;
c) about 15.7% by weight of microcrystalline cellulose;
d) about 3.0% by weight of colloidal silicon dioxide;
e) about 10.0% by weight of croscarmellose sodium intragranularly;

f) about 10.0% by weight of croscarmellose sodium extragranularly;
g) about 2.0% by weight of one or more sucrose fatty acid esters including sucrose palmitate;
h) about 4.0% by weight of hydroxypropyl methylcellulose; and
i) about 1.5% by weight of magnesium stearate,
wherein the total weight of components from a) to i) is 100%.

In some embodiments of any one of formulations as described above, the tablet formulation is a common blend formulation, wherein a ratio of CLTX-305 by weight to a total weight of one or more pharmaceutically acceptable excipients is constant across two or more dosage strengths. In some embodiments, a ratio of CLTX-305 by weight to a total weight of two or more pharmaceutically acceptable excipients is constant across two or more dosage strengths. In some embodiments, a ratio of CLTX-305 by weight to a total weight of three or more pharmaceutically acceptable excipients is constant across two or more dosage strengths. In some embodiments, a ratio of CLTX-305 by weight to a total weight of four or more pharmaceutically acceptable excipients is constant across two or more dosage strengths. In some embodiments, a ratio of CLTX-305 by weight to a total weight of five or more pharmaceutically acceptable excipients is constant across two or more dosage strengths. In some embodiments, a ratio of CLTX-305 by weight to a total weight of six or more pharmaceutically acceptable excipients is constant across two or more dosage strengths. In some embodiments, a ratio of CLTX-305 by weight to a total weight of seven or more pharmaceutically acceptable excipients is constant across two or more dosage strengths.

In another aspect, the present disclosure provides a tablet formulation as a common blend formulation across two or more dosage strengths. The common blend tablet formulation includes:
a) CLTX-305 represented by the formula:

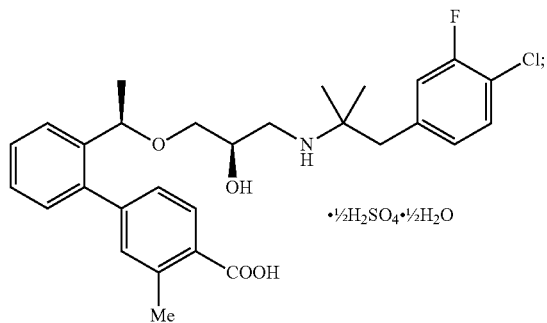 [SMILES: Cc1cc(-c2ccccc2[C@@H](C)OC[C@H](O)CNC(C)(C)Cc2ccc(Cl)c(F)c2)ccc1C(=O)O]

and
b) seven or more pharmaceutically acceptable excipients including a first filler, a second filler, a glidant, a disintegrant, a surfactant, a binder, and a lubricant,
wherein:
CLTX-305 is present in an amount of from about 13% to about 30% by weight;
the first filler is mannitol;
the second filler is microcrystalline cellulose;
the glidant is colloidal silicon dioxide;
the disintegrant is croscarmellose sodium;
the surfactant is one or more sucrose fatty acid esters comprising sucrose palmitate;
the binder is hydroxypropyl methylcellulose;
the lubricant is magnesium stearate; and
a ratio of the compound by weight to a total weight of the seven or more pharmaceutically acceptable excipients is constant across two or more dosage strengths.

In some embodiments, the common blend tablet formulation includes:
a) CLTX-305 represented by the formula:

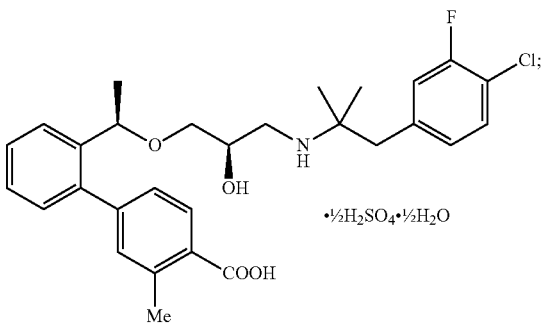 [SMILES: Cc1cc(-c2ccccc2[C@@H](C)OC[C@H](O)CNC(C)(C)Cc2ccc(Cl)c(F)c2)ccc1C(=O)O]

and
b) seven or more pharmaceutically acceptable excipients including a first filler, a second filler, a glidant, a disintegrant, a surfactant, a binder, and a lubricant,
wherein:
CLTX-305 is present in an amount of from about 13% to about 15% by weight;
the first filler is mannitol;
the second filler is microcrystalline cellulose;
the glidant is colloidal silicon dioxide;
the disintegrant is croscarmellose sodium;
the surfactant is one or more sucrose fatty acid esters comprising sucrose palmitate;
the binder is hydroxypropyl methylcellulose;
the lubricant is magnesium stearate; and
a ratio of the compound by weight to a total weight of the seven or more pharmaceutically acceptable excipients is constant across two or more dosage strengths.

In some embodiments of the common blend formulation, the tablet formulation is in two or more dosage strengths, where CLTX-305 is present in an amount of from about 5 to about 1000 mg in each tablet. In some embodiments, CLTX-305 is present in an amount of about 5 mg, about 10 mg, about 30 mg, about 60 mg, about 120 mg, about 240 mg, about 360 mg, or about 720 mg in each tablet.

In some embodiments of the common blend formulation, the ratio of CLTX-305 to one or more pharmaceutically acceptable excipients combined is from about 1:6.5 to about 1:5 by weight. In some embodiments, the ratio of CLTX-305 to one or more pharmaceutically acceptable excipients combined is about 1:6 by weight. In some embodiments, the ratio of CLTX-305 to one or more pharmaceutically acceptable excipients combined is about 1:6 by weight in all of three dosage strengths, wherein CLTX-305 is present in an amount of about 5 mg, about 10 mg, about 30 mg, about 60 mg, about 120 mg, about 240 mg, about 360 mg, or about 720 mg in each tablet.

In some embodiments of the common blend formulation, a ratio of mannitol to microcrystalline cellulose is no more than about 3. In some embodiments of the common blend formulation, mannitol and microcrystalline cellulose are present in an amount of from about 40% to about 70%, from about 40% to about 60%, from about 50% to about 70%, or from about 50% to about 60% by weight of the tablet formulation, wherein a ratio of mannitol to microcrystalline cellulose is no more than about 3. In some embodiments of the common blend formulation, mannitol and microcrystalline cellulose are present in an amount of from about 50% to about 60% by weight of the tablet formulation, wherein a ratio of mannitol to microcrystalline cellulose is no more than about 3. In some embodiments, mannitol and microcrystalline cellulose are present in an amount of about 55.2% by weight of the tablet formulation, wherein a ratio of mannitol to microcrystalline cellulose is about 2.5. In some embodiments, mannitol is present in an amount of from about 20% to about 60%, from about 30% to about 60%, or from about 30% to about 50% by weight of the tablet formulation. In some embodiments, mannitol is present in an amount of from about 30% to about 50% by weight of the tablet formulation. In some embodiments, mannitol is present in an amount of about 39.5% by weight of the tablet formulation. In some embodiments, microcrystalline cellulose is present in an amount of from about 10% to about 25% or from about 10% to about 20% by weight of the tablet formulation. In some embodiments, microcrystalline cellulose is present in an amount of from about 10% to about 20% by weight of the tablet formulation. In some embodiments, microcrystalline cellulose is present in an amount of about 15.7% by weight of the tablet formulation.

In some embodiments of the common blend formulation, colloidal silicon dioxide is present in an amount of from about 2% to about 4% by weight of the tablet formulation. In some embodiments, colloidal silicon dioxide is present in an amount of about 3.0% by weight of the tablet formulation.

In some embodiments of the common blend formulation, croscarmellose sodium is present in an amount of from about 10% to about 30%, from about 15% to about 30%, or from about 15% to about 25% by weight of the tablet formulation. In some embodiments, croscarmellose sodium is present in an amount of from about 15% to about 25% by weight of the tablet formulation. In some embodiments, croscarmellose sodium is present in an amount of about 20.0% by weight of the tablet formulation. In some embodiments, croscarmellose sodium is present intragranularly, extragranularly, or a combination thereof. In some embodiments, croscarmellose sodium is present both intragranularly and extragranularly. In some embodiments, croscarmellose sodium is present intragranularly in an amount of from about 5% to about 15% by weight of the tablet formulation. In some embodiments, croscarmellose sodium is present intragranularly in an amount of about 10.0% by weight of the tablet formulation. In some embodiments, croscarmellose sodium is present extragranularly in an amount of from about 5% to about 15% by weight of the tablet formulation. In some embodiments, croscarmellose sodium is present extragranularly in an amount of about 10.0% by weight of the tablet formulation.

In some embodiments of the common blend formulation, the one or more sucrose fatty acid esters are present in an amount of from about 1% to about 3% by weight of the tablet formulation. In some embodiments, the one or more sucrose fatty acid esters are present in an amount of about 2.0% by weight of the tablet formulation.

In some embodiments of the common blend formulation, hydroxypropyl methylcellulose is present in an amount of from about 3% to about 5% by weight of the tablet formulation. In some embodiments, hydroxypropyl methylcellulose is present in an amount of about 4.0% by weight of the tablet formulation.

In some embodiments of the common blend formulation, magnesium stearate is present extragranularly in an amount of from about 1% to about 2% by weight of the tablet formulation. In some embodiments, magnesium stearate is present extragranularly in an amount of from about 1% to about 2% by weight of the tablet formulation. In some embodiments, magnesium stearate is present extragranularly in an amount of about 1.5% by weight of the tablet formulation.

In some embodiments of the common blend formulation, the tablet formulation includes:
a) CLTX-305 represented by the formula:

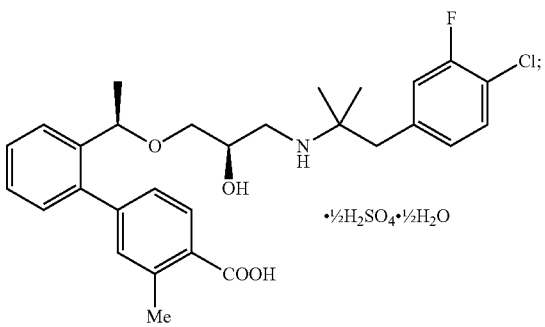 [SMILES: Cc1cc(-c2ccccc2[C@@H](C)OC[C@H](O)CNC(C)(C)Cc2ccc(Cl)c(F)c2)ccc1C(=O)O]

and
b) seven or more pharmaceutically acceptable excipients including a first filler, a second filler, a glidant, a disintegrant, a surfactant, a binder, and a lubricant,
wherein:
  CLTX-305 is present in an amount of about 14.3% by weight;
  the first filler is mannitol in an amount of about 39.5% by weight;
  the second filler is microcrystalline cellulose in an amount of about 15.7% by weight;
  the glidant is colloidal silicon dioxide in an amount of about 3.0% by weight;
  the disintegrant is croscarmellose sodium, which is present intragranularly in an amount of about 10.0% by weight and extragranularly in an amount of about 10.0% by weight;
  the surfactant is one or more sucrose fatty acid esters including sucrose palmitate, in an amount of about 2.0% by weight;
  the binder is hydroxypropyl methylcellulose in an amount of about 4.0% by weight; and
  the lubricant is magnesium stearate, which is present in an amount of about 1.5% by weight.

In some embodiments of any one of the formulations as described herein, the tablet is coated with a coating agent. Suitable coating agents include hypromellose, polyvinyl acetone, ethylcellulose, and polymethacrylates, as well as coating products such as those sold by OPADRY®. In some embodiments, the coating agent is Opadry® White Coating System, Opadry® coating system 03B680008 or equivalent, Opadry® Clear, Opadry® Blue 13B50579, Opadry® QX 321A180025, or Opadry® II (33G28707). In some embodiments, the coating agent is Opadry® White Coating System. In some embodiments, the coating agent is Opadry® White Coating System including hydroxypropyl methylcellulose, titanium dioxide, and Macrogol/PEG (MW 400). In some embodiments, the coating agent is Opadry® coating system 03B680008 or equivalent. For the purposes of calculating percent weight of the tablet formulation, the amount of coating agent is not included in the calculation. That is, the percent weights reported herein are of the uncoated tablet.

In some embodiments of any one of formulations as described herein, the tablet has a dissolution of at least about 75%, at least about 80%, at least about 85%, at least about 90%, or at least about 95% after about 60 minutes in a buffered solution of pH 6.8 containing sodium lauryl sulfate (SLS). In some embodiments, the tablet containing about 10 mg of CLTX-305 has a dissolution of at least about 90%, or at least about 95% after about 60 minutes in a buffered solution of pH 6.8 containing sodium lauryl sulfate (SLS). In some embodiments, the tablet containing about 10 mg of CLTX-305 has a dissolution of about 95% after about 60 minutes in a buffered solution of pH 6.8 containing sodium lauryl sulfate (SLS). In some embodiments, the tablet containing about 30 mg of CLTX-305 has a dissolution of at least about 90% or at least about 95% after about 60 minutes in a buffered solution of pH 6.8 containing sodium lauryl sulfate (SLS). In some embodiments, the tablet containing about 30 mg of CLTX-305 has a dissolution of at least about 90% after about 60 minutes in a buffered solution of pH 6.8 containing sodium lauryl sulfate (SLS). In some embodiments, the tablet containing about 60 mg of CLTX-305 has a dissolution of at least about 80%, at least about 85%, or at least about 90% after about 60 minutes in a buffered solution of pH 6.8 containing sodium lauryl sulfate (SLS). In some embodiments, the tablet containing about 60 mg of CLTX-305 has a dissolution of at least about 85% after about 60 minutes in a buffered solution of pH 6.8 containing sodium lauryl sulfate (SLS). In some embodiments, the tablet containing about 60 mg of CLTX-305 has a dissolution of at least about 90% after about 60 minutes in a buffered solution of pH 6.8 containing sodium lauryl sulfate (SLS).

In some embodiments of any one of formulations as described herein, the tablet has a maximum dissolution of near 100% after about 20, about 30, about 45, or about 60 minutes. In some embodiments of any one of formulations as described herein, the tablet has a maximum dissolution of about 95% after about 20, about 30, about 45, or about 60 minutes. In some embodiments, the tablet containing about 10 mg of CLTX-305 has a maximum dissolution of about 95% after about 20 or about 30 minutes. In some embodiments, the tablet containing about 10 mg of CLTX-305 has a maximum dissolution of about 95% after about 20 minutes. In some embodiments, the tablet containing about 30 mg of CLTX-305 has a maximum dissolution of about 95% after about 20 or about 30 minutes. In some embodiments, the tablet containing about 30 mg of CLTX-305 has a maximum dissolution of about 95% after about 20 minutes. In some embodiments, the tablet containing about 30 mg of CLTX-305 has a maximum dissolution of about 95% after about 30 minutes. In some embodiments, the tablet containing about 60 mg of CLTX-305 has a maximum dissolution of about 95% after about 20, about 30, about 45, or about 60 minutes. In some embodiments, the tablet containing about 60 mg of CLTX-305 has a maximum dissolution of about 95% after about 20 minutes. In some embodiments, the tablet containing about 60 mg of CLTX-305 has a maximum dissolution of about 95% after about 30 minutes. In some embodiments, the tablet containing about 60 mg of CLTX-305 has a maximum dissolution of about 95% after about 45 minutes. In some embodiments, the tablet containing about 60 mg of CLTX-305 has a maximum dissolution of about 95% after about 60 minutes.

The tablet formulations of the present disclosure exhibit good stability at storage conditions of either about 25° C./60% relative humidity (RH) or about 40° C./75% relative humidity (RH), during which no significant change is observed in impurities, assay (the content of the compound of formula (I)), dissolution, or tablet appearance. In some embodiments, the tablet is stable over a period of about 6 months at a temperature of about 40° C. and a relative humidity of about 75%. In some embodiments, the tablet is stable over a period of about 9 months at a temperature of about 25° C. and a relative humidity of about 60%. In some embodiments, the tablet is stable over a period of about one (1) year at a temperature of about 25° C. and a relative humidity of about 60%. In some embodiments, the tablet is stable over a period of about two (2) years at a temperature of about 25° C. and a relative humidity of about 60%. In some embodiments, the tablet is stable over a period of about three (3) years at a temperature of about 25° C. and a relative humidity of about 60%.

In some embodiments, the tablet containing about 10 mg of CLTX-305 is stable over a period of about 6 months at a temperature of about 40° C. and a relative humidity of about 75%, during which the content of the compound of formula (I) has a change of less than about 2%, about 1%, or about 0.5% relative to an initial content; and the dissolution of the tablet reaches at least about 90% after about 60 minutes in a buffered solution of pH 6.8 containing sodium lauryl sulfate (SLS). In some embodiments, the tablet containing about 10 mg of CLTX-305 is stable over a period of about 6 months at a temperature of about 40° C. and a relative humidity of about 75%, during which the content of the compound of formula (I) has a change of less than about 0.5% relative to an initial content; and the dissolution of the tablet reaches at least about 95% after about 60 minutes in a buffered solution of pH 6.8 containing sodium lauryl sulfate (SLS). In some embodiments, the tablet containing about 30 mg of CLTX-305 is stable over a period of about 6 months at a temperature of about 40° C. and a relative humidity of about 75%, during which the content of the compound of formula (I) has a change of less than about 5%, about 4%, about 3%, about 2%, or about 1% relative to an initial content; and the dissolution of the tablet reaches at least about 75% after about 60 minutes in a buffered solution of pH 6.8 containing sodium lauryl sulfate (SLS). In some embodiments, the tablet containing about 30 mg of CLTX-305 is stable over a period of about 6 months at a temperature of about 40° C. and a relative humidity of about 75%, during which the content of the compound of formula (I) has a change of less than about 1% relative to an initial content; and the dissolution of the tablet reaches at least about 80% after about 60 minutes in a buffered solution of pH 6.8 containing sodium lauryl sulfate (SLS). In some embodiments, the tablet containing about 60 mg of CLTX-305 is stable over a period of about 6 months at a temperature of about 40° C. and a relative humidity of about 75%, during which the content of the compound of formula (I) has a change of less than about 5%, about 4%, about 3%, about 2%, or about 1%, relative to an initial content; and the dissolution of the tablet reaches at least about 75% after about 60 minutes in a buffered solution of pH 6.8 containing sodium lauryl sulfate (SLS). In some embodiments, the tablet containing about 60 mg of CLTX-305 is stable over a period of about 6 months at a temperature of about 40° C. and a relative humidity of about 75%, during which the content of the compound of formula (I) has a change of less than about 3% relative to an initial content; and the dissolution of the tablet reaches at least about 80% after about 60 minutes in a buffered solution of pH 6.8 containing sodium lauryl sulfate (SLS).

In some embodiments, the tablet containing about 10 mg of CLTX-305 is stable over a period of about 9 months at a temperature of about 25° C. and a relative humidity of about 60%, during which the content of the compound of formula (I) has a change of less than about 2%, about 1%, or about 0.5% relative to an initial content; and the dissolution of the tablet reaches at least about 90% after about 60 minutes in a buffered solution of pH 6.8 containing sodium lauryl sulfate (SLS). In some embodiments, the tablet containing about 10 mg of CLTX-305 is stable over a period of about 9 months at a temperature of about 25° C. and a relative humidity of about 60%, during which the content of the compound of formula (I) has a change of less than about 0.5% relative to an initial content; and the dissolution of the tablet reaches at least about 95% after about 60 minutes in a buffered solution of pH 6.8 containing sodium lauryl sulfate (SLS). In some embodiments, the tablet containing about 30 mg of CLTX-305 is stable over a period of about 9 months at a temperature of about 25° C. and a relative humidity of about 60%, during which the content of the compound of formula (I) has a change of less than about 5%, about 4%, about 3%, about 2%, or about 1% relative to an initial content; and the dissolution of the tablet reaches at least about 75% after about 60 minutes in a buffered solution of pH 6.8 containing sodium lauryl sulfate (SLS). In some embodiments, the tablet containing about 30 mg of CLTX-305 is stable over a period of about 9 months at a temperature of 25° C. and a relative humidity of about 60%, during which the content of the compound of formula (I) has a change of less than about 1% relative to an initial content; and the dissolution of the tablet reaches at least about 80% after about 60 minutes in a buffered solution of pH 6.8 containing sodium lauryl sulfate (SLS). In some embodiments, the tablet containing about 60 mg of CLTX-305 is stable over a period of about 6 months at a temperature of about 25° C. and a relative humidity of 6 about 0%, during which the content of the compound of formula (I) has a change of less than about 5%, about 4%, about 3%, about 2%, or about 1%, relative to an initial content; and the dissolution of the tablet reaches at least about 75% after about 60 minutes in a buffered solution of pH 6.8 containing sodium lauryl sulfate (SLS). In some embodiments, the tablet containing about 60 mg of CLTX-305 is stable over a period of about 9 months at a temperature of 25° C. and a relative humidity of about 60%, during which the content of the compound of formula (I) has a change of less than about 3% relative to an initial content; and the dissolution of the tablet reaches at least about 80% after about 60 minutes in a buffered solution of pH 6.8 containing sodium lauryl sulfate (SLS).

IV. Method

In a third aspect, the present disclosure provides a method of treating autosomal dominant hypocalcemia (ADH, e.g., autosomal dominant hypocalcemia type 1 (ADH1)). The method includes administering to a subject in need thereof an effective amount of the tablet formulation including the compound of formula (I), a solvate, a hydrate, a pharmaceutically acceptable salt, or combinations thereof; and one or more pharmaceutically acceptable excipients selected from one or more fillers, one or more glidants, one or more disintegrants, one or more surfactants, one or more binders, one or more lubricants, and a combination thereof, wherein the compound of formula (I) is present in an amount of at least about 12% by weight, on a salt-free and anhydrous basis.

In some embodiments, the method includes administering to a subject in need thereof, an effective amount of the tablet formulation including:
a) CLTX-305 represented by the formula:

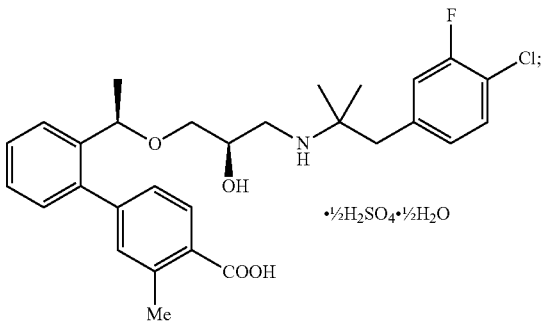 [SMILES: Cc1cc(-c2ccccc2[C@@H](C)OC[C@H](O)CNC(C)(C)Cc2ccc(Cl)c(F)c2)ccc1C(=O)O]

and
b) seven or more pharmaceutically acceptable excipients including a first filler, a second filler, a glidant, a disintegrant, a surfactant, a binder, and a lubricant, wherein:
CLTX-305 is present in an amount of from about 13% to about 30% by weight;
the first filler is mannitol;
the second filler is microcrystalline cellulose;
the glidant is colloidal silicon dioxide;
the disintegrant is croscarmellose sodium;
the surfactant is one or more sucrose fatty acid esters comprising sucrose palmitate;
the binder is hydroxypropyl methylcellulose;
the lubricant is magnesium stearate; and
a ratio of the compound by weight to a total weight of the seven or more pharmaceutically acceptable excipients is constant across two or more dosage strengths.

In some embodiments, the method includes administering to a subject in need thereof, an effective amount of the tablet formulation including:
a) CLTX-305 represented by the formula:

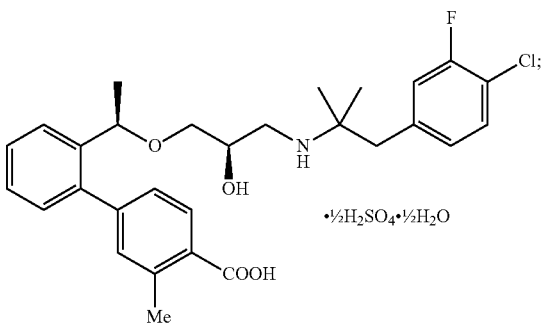 [SMILES: Cc1cc(-c2ccccc2[C@@H](C)OC[C@H](O)CNC(C)(C)Cc2ccc(Cl)c(F)c2)ccc1C(=O)O]

and
b) seven or more pharmaceutically acceptable excipients including a first filler, a second filler, a glidant, a disintegrant, a surfactant, a binder, and a lubricant, wherein:
CLTX-305 is present in an amount of from about 13% to about 15% by weight;
the first filler is mannitol;
the second filler is microcrystalline cellulose;
the glidant is colloidal silicon dioxide;

the disintegrant is croscarmellose sodium;
the surfactant is one or more sucrose fatty acid esters comprising sucrose palmitate;
the binder is hydroxypropyl methylcellulose;
the lubricant is magnesium stearate; and
a ratio of the compound by weight to a total weight of the seven or more pharmaceutically acceptable excipients is constant across two or more dosage strengths.

In some embodiments, the ADH is autosomal dominant hypocalcemia type 1 (ADH1).

In some embodiments, the subject has hypocalcemia, hyperphosphatemia, and/or hypercalciuria. In some embodiments, the subject has hypocalcemia. In some embodiments, the subject has hyperphosphatemia. In some embodiments, the subject has hypercalciuria. In some embodiments, the subject has hypocalcemia and hypercalciuria. In some embodiments, the subject has hypocalcemia, hyperphosphatemia, and hypercalciuria. In some embodiments, the subject has previously been diagnosed with ADH1. In some embodiments, the subject has previously undergone treatment for ADH1.

In some embodiments, the tablet formulation including the compound of formula (I) is administered orally.

In some embodiments, the method includes administering to a subject in need thereof, an effective amount of the tablet formulation including:
a) CLTX-305; and
b) seven or more pharmaceutically acceptable excipients including a first filler, a second filler, a glidant, a disintegrant, a surfactant, a binder, and a lubricant,
wherein:
CLTX-305 is present in an amount of about 14.3% by weight;
the first filler is mannitol in an amount of about 39.5% by weight;
the second filler is microcrystalline cellulose in an amount of about 15.7% by weight;
the glidant is colloidal silicon dioxide in an amount of about 3.0% by weight;
the disintegrant is croscarmellose sodium, which is present intragranularly in an amount of about 10.0% by weight and extragranularly in an amount of about 10.0% by weight;
the surfactant is one or more sucrose fatty acid esters including sucrose palmitate, in an amount of about 2.0% by weight;
the binder is hydroxypropyl methylcellulose in an amount of about 4.0% by weight; and
the lubricant is magnesium stearate, which is present in an amount of about 1.5% by weight.

In some embodiments, the tablet formulation is about 10 mg, about 30 mg, about 60 mg, about 120 mg, about 240 mg, about 360 mg, or about 720 mg tablet, wherein CLTX-305 is present in an amount of about 5 mg, about 10 mg, about 30 mg, about 60 mg, about 120 mg, about 240 mg, about 360 mg, or about 720 mg in each tablet.

In some embodiments, the effective amount of the tablet formulation including the compound of formula (I) (e.g., CLTX-305) increases a blood calcium concentration (cCa) to a normal range. In some embodiments, the effective amount of the tablet formulation including the compound of formula (I) (e.g., CLTX-305) mitigates symptoms associate with hypocalcemia.

In some embodiments, the effective amount of the tablet formulation including the compound of formula (I) (e.g., CLTX-305) increases intact parathyroid hormone (iPTH) in blood to a normal range.

In some embodiments, the effective amount of the tablet formulation including the compound of formula (I) (e.g., CLTX-305) decreases an elevated urinary calcium level. In some embodiments, the effective amount of the tablet formulation including the compound of formula (I) (e.g., CLTX-305) increases a urinary calcium clearance. In some embodiments, the effective amount of the tablet formulation including the compound of formula (I) (e.g., CLTX-305) minimizes the extent of hypercalciuria.

In some embodiments, the effective amount of the tablet formulation including the compound of formula (I) (e.g., CLTX-305) decreases a blood phosphate level to a normal range. In some embodiments, the effective amount of the tablet formulation including the compound of formula (I) (e.g., CLTX-305) minimizes the extent of hyperphosphatemia.

In some embodiments, the effective amount of the tablet formulation including the compound of formula (I) (e.g., CLTX-305) increases a blood magnesium level to a normal range. In some embodiments, the effective amount of the tablet formulation including the compound of formula (I) (e.g., CLTX-305) minimizes the extent of hypomagnesium.

The treatment method of the present disclosure may be administered alone or in conjunction with another form of pharmaceutical therapy, e.g., a second compound having a calcium-sensing receptor antagonistic action, vitamin D supplement, and/or a calcium supplement. In some embodiments, the method further includes administering an oral calcium supplement. In some embodiments, "in conjunction with" means that the tablet formulations of the present disclosure and another pharmaceutical agent are administered to a subject as part of a treatment regimen or plan. In some embodiments, being used in conjunction does not require that the tablet formulations of the present disclosure and another pharmaceutical agent are physically combined prior to administration or that they be administered over the same time frame.

V. Examples

Analytical Procedures

The analytical methods used for testing of 10 mg, 30 mg, and 60 mg tablets were identical. A summary of analytical procedures is provided below.

Appearance: A visual assessment of the tablet formulations was conducted for appearance testing.

Identification, Assay, Content Uniformity by HPLC: The tablet formulation identity, assay, and content uniformity were determined by a gradient reverse-phase HPLC method. This method utilizes a C18 column with gradient elution using mobile phases of 0.10% (volume/volume, v/v) trifluoroacetic acid (TFA) in water and 0.1% TFA in 50/50 (v/v) acetonitrile and tetrahydrofuran. The ultraviolet (UV) detection is performed at 220 nanometers (nm). Content uniformity was determined per USP<905>.

Related Substances: The levels of related substances for the tablet formulations were determined by a gradient reverse-phase HPLC method. This method utilizes a C18 column with gradient elution using mobile phases of 0.10% (v/v) trifluoroacetic acid (TFA) in water and 0.10% TFA in 50/50 (v/v) acetonitrile and tetrahydrofuran. The UV detection is performed at 220 nm. This method is similar to the Identification, Assay, Content Uniformity by HPLC, with the main difference being the longer method run time in order to afford higher resolution for related substance peaks.

Dissolution Determination by HPLC: A standard USP type 2 (Paddle) apparatus was used with the paddle speed of 50 RPM or 75 RPM in accordance with USP <711>. The dissolution method utilizes a buffered solution (pH 6.8) containing sodium lauryl sulfate (SLS) as the dissolution media to create sink conditions for the Tablets. Samples were analyzed by a gradient reverse-phase HPLC method with a C18 column. A standard quantitation was performed to determine the sample concentration.

Water Content: Water content was determined by volumetric KF titration in accordance with USP<921>.

Microbial Limit Testing: Microbial examination was performed in accordance with USP<61> and USP<62>.

Example 1: Preparation of Tablet Formulations

Table 1 lists the composition of a tablet formulations. Table 2 lists the composition of a suitable Opadry® Film Coating System. Other coating systems may also be suitable.

TABLE 2

Composition of an Opadry Film Coating System[1]

| Excipient | Quality Standard |
|---|---|
| Hydroxypropyl Methylcellulose | USP, CFR (172.874), EP, JP |
| Titanium Dioxide | USP, CFR (73.57573.1575), EP, JP |
| Macrogol/PEG (MW 400) | NF, CFR (172.820), EP, JP |

[1]Opadry coating system 03B680008 or equivalent can be used.

The tablets including the compound of formula (I) (e.g., CLTX-305) and pharmaceutically acceptable excipients were prepared according the following steps.

Step-1: Dispensing

CLTX-305 and the excipients were weighed according to the composition of Table 1 and then sieved through a screen before use in manufacturing of the tablets of the present disclosure.

Step-2: Fluid Bed Granulation

The hydroxypropyl methylcellulose and sucrose fatty acid esters were mixed with purified water to form the binder solution prior to the initiation of the fluid bed granulation operation.

CLTX-305, mannitol, microcrystalline cellulose, colloidal silicon dioxide, and croscarmellose sodium were charged to the fluid bed granulator. The granulation operation included the following steps: a preheating/pre-mixing by fluidizing the powder before initiation of spraying of the binder, spraying of the binder solution, drying, and delumping.

Based on the batch size for a given batch, the fluid bed granulation operation can be performed in sub-lots. The granulation sublots were combined prior to initiation of the final blend.

TABLE 1

Composition of the Tablet Formulations

| Components | Function | Composition (% weight) | 10 mg/ tablet | 30 mg/ tablet | 60 mg/ tablet |
|---|---|---|---|---|---|
| Intragranular | | | | | |
| CLTX-305 | Active Ingredient | 14.3 | 10.0 | 30.0 | 60.0 |
| Mannitol | Filler | 39.5 | 27.6 | 82.9 | 165.9 |
| Microcrystalline Cellulose | Filler | 15.7 | 11.0 | 33.0 | 66.0 |
| Colloidal Silicon Dioxide | Glidant | 3.0 | 2.1 | 6.3 | 12.6 |
| Croscarmellose Sodium | Disintegrant | 10.0 | 7.0 | 21.0 | 42.0 |
| Sucrose Fatty Acids Esters | Surfactant | 2.0 | 1.4 | 4.2 | 8.4 |
| Hydroxypropyl Methylcellulose | Binder | 4.0 | 2.8 | 8.4 | 16.8 |
| Purified Water[1] | Processing Agent | | | | |
| Extragranular | | | | | |
| Croscarmellose Sodium | Disintegrant | 10.0 | 7.0 | 21.0 | 42.0 |
| Magnesium Stearate | Lubricant | 1.5 | 1.1 | 3.2 | 6.3 |
| | Core Tablet Total | 100 | 70 | 210.0 | 420.0 |
| | pFilm Coat | | | | |
| Opadry White Coating System (Color coating)[2] | Cosmetic coat | 4.0 | 2.8 | 8.4 | 16.8 |
| | Total Coated Tablet | 104 | 72.8 | 218.4 | 436.8 |

[1]Removed during processing
[2]The components of Opadry coating system conform to the USP or NF compendial standards
[3]Complies with the USP criteria for Sucrose Palmitate Step-3: Final Blend The granulation from the fluid bed granulation operation was charged into a blender bin, if the batch consisted of sublots of granulation, all sublots were added to the blender bin. The extragranular excipients, croscarmellose sodium and magnesium stearate, were sieved and then charged to the blender bin and the final blending was performed.

Step-4: Compression

The final blend was compressed into tablets using a tablet press and the tablets were dedusted and metal detected after compression. Core tablets were tested for weight uniformity, hardness, thickness, and friability.

Step-5: Coating

The tablet cores were coated in a pan coater with a suspension of Opadry® white in purified water, using an aqueous spray system, then dried in the coater. Tablets were monitored for weight gain during the coating process.

Step-6: Packaging

Thirty tablets along with a desiccant are packaged in high-density polyethylene (HDPE) bottles. Each bottle was induction sealed and enclosed with a child-resistant polypropylene cap. Tablet count, induction seal integrity and cap torque on were checked throughout the packaging process.

Step-7: Labelling

Filled bottles were labelled with the approved labels.

Example 2: Dissolution of Tablets

The dissolution of tablets including 10 mg, 30 mg, and 60 mg CLTX-305 were performed in a buffered solution (pH 6.8) containing sodium lauryl sulfate (SLS) as the dissolution media according to the dissolution method as described above.

As shown in FIG. 1, all tablet strengths reached plateau for maximum dissolution by approximately 20 minutes.

Example 3: Stability of Tablet Formulations (non-GMP Batch)

10 mg and 60 mg CLTX-305 tablets were used to assess stability of the formulation. Given that the tablet formulation in the present application is a common blend, the stability study brackets the 30 mg dosage strength tablet. Stability data from the stability study were available for up to six (6) months storage at an accelerated storage condition of 40° C./75% Relative Humidity (RH), and for up to twelve (12) months storage at a long-term storage condition of 25° C./60% RH. Stability may be assessed at additional test intervals of, e.g., 3 months and 6 months. Stability data for appearance, assay, total impurities, and dissolution are presented in Table 3 through Table 6. No significant change was observed in impurities, assay, dissolution, or tablet appearance at storage conditions of either 25° C./60% RH or 40° C./75% RH.

TABLE 3

Stability of 10 mg Tablet at 25° C./60% RH

| Test | | Initial | | 12 Months | |
|---|---|---|---|---|---|
| Appearance | | White film-coated tablet | | White film-coated tablet | |
| Assay of AI content[1] | | 105.5% | | 104.0% | |
| | Time | Mean (%) (50 rpm) | — | Mean (%) (50 rpm) | Mean (%) (75 rpm) |
| Dissolution | 10 min | 69% | — | 60% | 97% |
| | 15 min | 89% | — | 86% | 100% |
| | 20 min | 96% | — | 96% | 100% |
| | 30 min | 99% | — | 100% | 100% |
| | 45 min | 100% | — | 101% | 101% |
| | 60 min | 100% | — | 101% | 101% |
| | 75 min | 99% | — | 101% | 101% |
| Related Substances (% w/w) | Each Impurity | RRT 0.93 | 0.14% | RRT 0.93 | 0.13% |
| | | RRT 1.09 | 0.13% | RRT 1.09 | 0.08% |
| | Total Impurities | 0.28% | | 0.21% | |
| | Water content (%) | 3.2% | | 2.7% | |
| | Content uniformity | Meet the criteria of USP <905> | | Not tested | |

[1] AI content refers to the content of the compound of formula (I) as the Active Ingredient (AI), determined by a HPLC method

TABLE 4

Stability of 10 mg Tablet at 40° C./75% RH

| Test | | Initial | 6 Months |
|---|---|---|---|
| Appearance | | White film-coated tablet | White film-coated tablet |
| Assay of AI content[1] | | 105.5% | 105.2% |
| | Time | Mean (%) (50 rpm) | Mean (%) (50 rpm) |
| Dissolution | 10 min | 69% | 53% |
| | 15 min | 89% | 84% |
| | 20 min | 96% | 97% |
| | 30 min | 99% | 101% |

TABLE 4-continued

Stability of 10 mg Tablet at 40° C./75% RH

| Test | | Initial | | 6 Months | |
|---|---|---|---|---|---|
| | 45 min | 100% | | 103% | |
| | 60 min | 100% | | 102% | |
| | 75 min | 99% | | 103% | |
| Related | Each Impurity | RRT 0.93 | 0.14% | RRT 0.93 | 0.14% |
| Substances | | RRT 1.09 | 0.13% | RRT 1.09 | 0.11% |
| (% w/w) | Total Impurities | 0.28% | | 0.25% | |
| | Water content (%) | 3.2% | | 1.9% | |
| | Content uniformity | Meet the criteria of USP <905> | | Not tested | |

[1] AI content refers to the content of the compound of formula (I) as the Active Ingredient (AI), determined by a HPLC method

TABLE 5

Stability of 60 mg Tablet at 25° C./60% RH

| Test | | Initial | | 12 Months | |
|---|---|---|---|---|---|
| Appearance | | White film-coated tablet | | White film-coated tablet | |
| Assay of AI content[1] | | 101.3% | | 99.2% | |
| | Time | Mean (%) (50 rpm) | — | Mean (%) (50 rpm) | Mean (%) (75 rpm) |
| Dissolution | 10 min | 25% | — | 29% | 65% |
| | 15 min | 66% | — | 65% | 95% |
| | 20 min | 88% | — | 90% | 98% |
| | 30 min | 97% | — | 97% | 98% |
| | 45 min | 99% | — | 97% | 98% |
| | 60 min | 100% | — | 97% | 98% |
| | 75 min | 101% | — | 97% | 98% |
| Related | Each Impurity | RRT 0.93 | 0.13% | RRT 0.93 | 0.12% |
| Substances | | RRT 1.09 | 0.11% | RRT 1.09 | 0.09% |
| (% w/w) | Total Impurities | 0.24% | | 0.20% | |
| | Water content (%) | 3.1% | | 2.7% | |
| | Content uniformity | Meet the criteria of USP <905> | | Not tested | |

[1] AI content refers to the content of the compound of formula (I) as the Active Ingredient (AI), determined by a HPLC method

TABLE 6

Stability of 60 mg Tablet at 40° C./75% RH

| Test | | Initial | | 6 Months | |
|---|---|---|---|---|---|
| Appearance | | White film-coated tablet | | White film-coated tablet | |
| Assay of AI content[1] | | 105.5% | | 105.2% | |
| | Time | Mean (%) (50 rpm) | | Mean (%) (50 rpm) | |
| Dissolution | 10 min | 25% | | 21% | |
| | 15 min | 66% | | 52% | |
| | 20 min | 88% | | 81% | |
| | 30 min | 97% | | 91% | |
| | 45 min | 99% | | 94% | |
| | 60 min | 100% | | 94% | |
| | 75 min | 101% | | 94% | |
| Related | Each Impurity | RRT 0.93 | 0.13% | RRT 0.93 | 0.14% |
| Substances | | RRT 1.09 | 0.11% | RRT 1.09 | 0.12% |
| (% w/w) | Total Impurities | 0.24% | | 0.25% | |
| | Water content (%) | 3.1% | | 2.2% | |
| | Content uniformity | Meet the criteria of USP <905> | | Not tested | |

[1] AI content refers to the content of the compound of formula (I) as the Active Ingredient (AI), determined by a HPLC method Example 4: Stability of Tablet Formulations (GMP Batch)

10 mg, 30 mg, and 60 mg CLTX-305 tablets were used to assess stability of the formulation. Stability data from the stability study were available for up to six (6) months storage at an accelerated storage condition of 40° C./75% o Relative Humidity (RH), and for up to nine (9) months storage at a long-term storage condition of 25° C./60% RH. Stability may be assessed at additional test intervals at 3 months and 6 months. Stability data for appearance, assay, total impurities, and dissolution were presented in Table 7 through Table 12. No significant change was observed in impurities, assay, dissolution, or tablet appearance at storage conditions of either 25° C./60%$_0$ RH or 40° C./75%$_0$ RH.

TABLE 7

Stability of 10 mg Tablet at 25° C./60% RH

| Test | | Initial | 9 Months |
|---|---|---|---|
| Appearance | | White film-coated tablet | White film-coated tablet |
| Assay of AI content[1] | | 102.2% | 103.6% |
| | Time | Mean (%) (75 rpm) | Mean (%) (75 rpm) |
| Dissolution | 10 min | 92% | 93% |
| | 15 min | 97% | 96% |
| | 20 min | 97% | 96% |
| | 30 min | 97% | 97% |
| | 45 min | 97% | 97% |
| | 60 min | 97% | 96% |
| | 75 min | 97% | 97% |
| Impurity (% w/w) | E4 impurity[2] | <0.1% | <0.1% |
| | D impurity[2] | <0.1% | <0.1% |
| | RRT 0.95 | <0.1% | <0.1% |
| | Unspecified impurities | No single unspecified impurity >0.1% | No single unspecified impurity >0.1% |
| | Total Impurities | <0.1% | <0.1% |
| | Water content (%) | 3.2% | 2.2% |

[1] AI content refers to the content of the compound of formula (I) as the Active Ingredient (AI), determined by a HPLC method; and
[2] Specified impurities

TABLE 8

Stability of 10 mg Tablet at 40° C./75% RH

| Test | | Initial | 6 Months |
|---|---|---|---|
| Appearance | | White film-coated tablet | White film-coated tablet |
| Assay of AI content[1] | | 102.2% | 104.0% |
| | Time | Mean (%) (75 rpm) | Mean (%) (75 rpm) |
| Dissolution | 10 min | 92% | 92% |
| | 15 min | 97% | 97% |
| | 20 min | 97% | 97% |
| | 30 min | 97% | 98% |
| | 45 min | 97% | 99% |
| | 60 min | 97% | 98% |
| | 75 min | 97% | 97% |
| Impurity (% w/w) | E4 impurity[2] | <0.1% | <0.1% |
| | D impurity[2] | <0.1% | <0.1% |
| | RRT 0.95 | <0.1% | <0.1% |
| | Unspecified impurities | No single unspecified impurity >0.1% | No single unspecified impurity >0.1% |
| | Total Impurities | <0.1% | <0.1% |
| | Water content (%) | 3.2% | 1.8% |

[1] AI content refers to the content of the compound of formula (I) as the Active Ingredient (AI), determined by a HPLC method; and
[2] Specified impurities

TABLE 9

Stability of 30 mg Tablet at 25° C./60% RH

| | Test | Initial | 9 Months |
|---|---|---|---|
| | Appearance | White film-coated tablet | White film-coated tablet |
| | Assay of AI content[1] | 99.9% | 102.3% |
| | Time | Mean (%) (75 rpm) | Mean (%) (75 rpm) |
| Dissolution | 10 min | 50% | 51% |
| | 15 min | 94% | 85% |
| | 20 min | 98% | 98% |
| | 30 min | 98% | 98% |
| | 45 min | 98% | 98% |
| | 60 min | 99% | 98% |
| | 75 min | 99% | 98% |
| Impurity (% w/w) | E4 impurity[2] | <0.1% | <0.1% |
| | D impurity[2] | <0.1% | <0.1% |
| | RRT 0.95 | <0.1% | <0.1% |
| | Unspecified impurities | No single unspecified impurity >0.1% | No single unspecified impurity >0.1% |
| | Total Impurities | <0.1% | <0.1% |
| | Water content (%) | 2.7% | 2.9% |

[1]AI content refers to the content of the compound of formula (I) as the Active Ingredient (AI), determined by a HPLC method; and
[2]Specified impurities

TABLE 10

Stability of 30 mg Tablet at 40° C./75% RH

| | Test | Initial | 6 Months |
|---|---|---|---|
| | Appearance | White film-coated tablet | White film-coated tablet |
| | Assay of AI content[1] | 99.9% | 102.3% |
| | Time | Mean (%) (75 rpm) | Mean (%) (75 rpm) |
| Dissolution | 10 min | 50% | 38% |
| | 15 min | 94% | 71% |
| | 20 min | 98% | 93% |
| | 30 min | 98% | 98% |
| | 45 min | 98% | 99% |
| | 60 min | 99% | 98% |
| | 75 min | 99% | 99% |
| Impurity (% w/w) | E4 impurity[2] | <0.1% | <0.1% |
| | D impurity[2] | <0.1% | <0.1% |
| | RRT 0.95 | <0.1% | <0.1% |
| | Unspecified impurities | No single unspecified impurity >0.1% | No single unspecified impurity >0.1% |
| | Total Impurities | <0.1% | <0.1% |
| | Water content (%) | 2.7% | 1.9% |

[1]AI content refers to the content of the compound of formula (I) as the Active Ingredient (AI), determined by a HPLC method; and
[2]Specified impurities

TABLE 11

Stability of 60 mg Tablet at 25° C./60% RH

| | Test | Initial | 9 Months |
|---|---|---|---|
| | Appearance | White film-coated tablet | White film-coated tablet |
| | Assay of AI content[1] | 99.4% | 101.0% |
| | Time | Mean (%) (75 rpm) | Mean (%) (75 rpm) |
| Dissolution | 10 min | 55% | 51% |
| | 15 min | 77% | 82% |
| | 20 min | 96% | 99% |
| | 30 min | 98% | 100% |
| | 45 min | 98% | 100% |
| | 60 min | 98% | 100% |
| | 75 min | 97% | 100% |
| Impurity (% w/w) | E4 impurity[2] | <0.1% | <0.1% |
| | D impurity[2] | <0.1% | <0.1% |
| | RRT 0.95 | <0.1% | <0.1% |
| | Unspecified impurities | No single unspecified impurity >0.1% | No single unspecified impurity >0.1% |
| | Total Impurities | <0.1% | <0.1% |
| | Water content (%) | 2.9% | 2.8% |

[1]AI content refers to the content of the compound of formula (I) as the Active Ingredient (AI), determined by a HPLC method; and
[2]Specified impurities

TABLE 12

Stability of 60 mg Tablet at 40° C./75% RH

| | Test | Initial | 6 Months |
|---|---|---|---|
| | Appearance | White film-coated tablet | White film-coated tablet |
| | Assay of AI content[1] | 99.9% | 100.5% |
| | Time | Mean (%) (75 rpm) | Mean (%) (75 rpm) |
| Dissolution | 10 min | 55% | 53% |
| | 15 min | 77% | 71% |
| | 20 min | 96% | 92% |
| | 30 min | 98% | 98% |
| | 45 min | 98% | 99% |
| | 60 min | 98% | 99% |
| | 75 min | 97% | 98% |
| Impurity (% w/w) | E4 impurity[2] | <0.1% | <0.1% |
| | D impurity[2] | <0.1% | <0.1% |
| | RRT 0.95 | <0.1% | <0.1% |
| | Unspecified impurities | No single unspecified impurity >0.1% | No single unspecified impurity >0.1% |
| | Total Impurities | <0.1% | <0.1% |
| | Water content (%) | 2.9% | 2.0% |

[1]AI content refers to the content of the compound of formula (I) as the Active Ingredient (AI), determined by a HPLC method; and
[2]Specified impurities Although the foregoing disclosure has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A tablet formulation comprising:
a compound represented by formula (I):

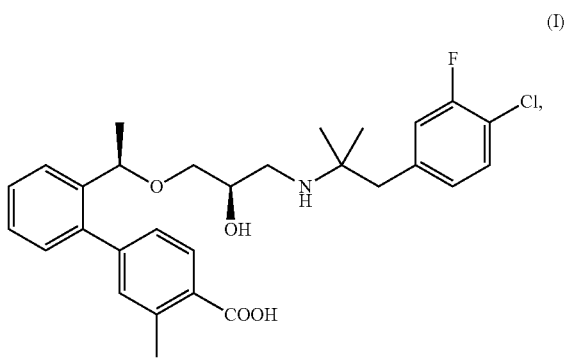 [SMILES: Cc1cc(-c2ccccc2[C@@H](C)OC[C@H](O)CNC(C)(C)Cc2ccc(Cl)c(F)c2)ccc1C(=O)O]

a solvate, a hydrate, or a pharmaceutically acceptable salt thereof, or a combination thereof;
mannitol and microcrystalline cellulose in a combined amount of from about 50% to about 70% by weight of the tablet formulation;
colloidal silicon dioxide in an amount of from about 1% to about 4% by weight of the tablet formulation;
croscarmellose sodium in an amount of from about 10% to about 30% by weight of the tablet formulation;
hydroxypropyl methylcellulose in an amount of from about 2% to about 5% by weight of the tablet formulation; and
magnesium stearate in an amount of from about 1% to about 2% by weight of the tablet formulation.

2. The tablet formulation of claim 1, wherein the compound of formula (I) is present in an amount of from about 12% to about 32% by weight of the tablet formulation, on a salt-free and anhydrous basis.

3. The tablet formulation of claim 1, wherein the compound of formula (I) is present in an amount of from about 12% to about 15% by weight of the tablet formulation, on a salt-free and anhydrous basis.

4. The tablet formulation of claim 1, wherein the compound of formula (I) is a hemihydrate hemisulfate salt.

5. The tablet formulation of claim 4, wherein the hemihydrate hemisulfate salt of the compound of formula (I) is present in an amount of from about 13% to about 35% by weight of the tablet formulation.

6. The tablet formulation of claim 4, wherein the hemihydrate hemisulfate salt of the compound of formula (I) is present in an amount of about 14.3% by weight of the tablet formulation.

7. The tablet formulation of claim 1, wherein at least about 75% of the compound of formula (I) is released from the tablet formulation after about 60 minutes in a buffered solution of pH 6.8 containing sodium lauryl sulfate.

8. The tablet formulation of claim 1, wherein at least about 80% of the compound of formula (I) is released from the tablet formulation after about 60 minutes in a buffered solution of pH 6.8 containing sodium lauryl sulfate.

9. The tablet formulation of claim 1, wherein at least about 85% of the compound of formula (I) is released from the tablet formulation after about 60 minutes in a buffered solution of pH 6.8 containing sodium lauryl sulfate.

10. The tablet formulation of claim 1, wherein at least about 90% of the compound of formula (I) is released from the tablet formulation after about 60 minutes in a buffered solution of pH 6.8 containing sodium lauryl sulfate.

11. The tablet formulation of claim 1, wherein at least about 95% of the compound of formula (I) is released from the tablet formulation after about 60 minutes in a buffered solution of pH 6.8 containing sodium lauryl sulfate.

* * * * *